(12) United States Patent
Fagan

(10) Patent No.: US 8,434,421 B2
(45) Date of Patent: May 7, 2013

(54) MANUALLY SETTABLE TAMPER RESISTANT INDICATOR DEVICE

(76) Inventor: Janet L. Fagan, Mountain View, CA (US)

(*) Notice: Subject to any disclaimer, the term of this patent is extended or adjusted under 35 U.S.C. 154(b) by 355 days.

(21) Appl. No.: 12/884,350

(22) Filed: Sep. 17, 2010

(65) Prior Publication Data

US 2011/0067623 A1  Mar. 24, 2011

Related U.S. Application Data

(60) Provisional application No. 61/244,818, filed on Sep. 22, 2009.

(51) Int. Cl.
*G09F 9/40* (2006.01)
*G09F 11/04* (2006.01)

(52) U.S. Cl.
USPC .......... 116/309; 116/308; 116/311; 116/321; 116/324

(58) Field of Classification Search ................ 116/306, 116/307, 308, 309, 311, 315, 316, 321, 323, 116/324; 206/459.1; 283/65, 79, 81; 40/5, 40/488, 490, 491, 492
See application file for complete search history.

(56) References Cited

U.S. PATENT DOCUMENTS

| | | | |
|---|---|---|---|
| 1,146,737 A | | 7/1915 | Senior |
| 1,317,660 A | * | 9/1919 | Carlson ........................ 116/308 |
| 2,974,433 A | * | 3/1961 | Litzinger ....................... 40/490 |
| 3,200,517 A | * | 8/1965 | Agostino ....................... 434/174 |
| 3,703,778 A | | 11/1972 | Pfleger |
| 3,910,032 A | | 10/1975 | Funaki et al. |
| 3,950,871 A | * | 4/1976 | Rege ............................... 40/492 |
| 4,022,376 A | | 5/1977 | Weber |
| 4,041,893 A | | 8/1977 | Mulloy |
| 4,075,771 A | | 2/1978 | Landsinger et al. |
| 4,208,984 A | * | 6/1980 | Glanzman ..................... 116/307 |
| 4,303,242 A | | 12/1981 | Ohki |
| 4,433,929 A | * | 2/1984 | Jones ............................. 402/14 |
| 4,461,497 A | | 7/1984 | Downey |
| 4,466,150 A | * | 8/1984 | Jurt ............................... 15/143.1 |
| 4,582,018 A | | 4/1986 | Fleck et al. |
| 4,656,765 A | * | 4/1987 | DeBoer ........................... 40/491 |
| 4,660,309 A | * | 4/1987 | LaRocca ........................... 40/5 |
| 4,920,912 A | | 5/1990 | Kirkling |
| 5,009,338 A | | 4/1991 | Barker |
| 5,102,167 A | * | 4/1992 | Groswith, III ................. 281/28 |
| 5,377,614 A | | 1/1995 | Glazer |
| 5,437,635 A | | 8/1995 | Fields et al. |
| 5,629,677 A | | 5/1997 | Staino, Jr. |

(Continued)

*Primary Examiner* — R. A. Smith

(74) *Attorney, Agent, or Firm* — Schneck & Schneck; David M. Schneck

(57) ABSTRACT

A manually settable, tamper resistant indicator device suitable for use in medical and other professions, and a method for operating the device, are disclosed. An indicia member is manually moved relative to a pointer member, in setting the indicator device to display selected indicia at a pointing area. The displayed information is locked by fixing the indicia member relative to the pointer member, using a tamper resistant locking member. A fastening device, which may be tamper resistant, is used for attaching the indicator device to an article, which may be a medical device attached to a medical patient. The indicator device may be sterilized. In a medical setting, the displayed information may include a day, a date, a usage count or a personnel identifier. In one example, the indicia member has a plurality of sliding strips, each sliding strip being mounted to the pointer member and independently movable.

41 Claims, 13 Drawing Sheets

U.S. PATENT DOCUMENTS

| | | | |
|---|---|---|---|
| 5,687,763 A | 11/1997 | Steinke | |
| 5,730,418 A | 3/1998 | Feith et al. | |
| 5,971,436 A | 10/1999 | Cox | |
| 6,119,990 A | 9/2000 | Kump et al. | |
| 6,496,831 B1 | 12/2002 | Baulier et al. | |
| 6,543,161 B2 | 4/2003 | Chin | |
| 6,641,533 B2 | 11/2003 | Causey, III et al. | |
| 6,802,279 B1 * | 10/2004 | Johnson | 116/306 |
| 6,938,768 B2 | 9/2005 | Ferretti et al. | |
| 6,951,353 B2 | 10/2005 | Kozlowski et al. | |
| 7,000,791 B2 | 2/2006 | Miller | |
| 7,123,149 B2 | 10/2006 | Nowak et al. | |
| 7,314,022 B2 | 1/2008 | Sollaccio | |
| 7,319,395 B2 | 1/2008 | Puzio et al. | |
| 7,357,792 B2 | 4/2008 | Newton et al. | |
| 7,661,384 B2 * | 2/2010 | Mataya | 116/311 |
| 2005/0044759 A1 | 3/2005 | Schweikert | |
| 2005/0160641 A1 * | 7/2005 | Camacho et al. | 40/492 |
| 2006/0236578 A1 * | 10/2006 | Saint et al. | 40/633 |
| 2009/0114729 A1 | 5/2009 | Conner et al. | |
| 2009/0139516 A1 | 6/2009 | Augustyn et al. | |
| 2009/0264866 A1 | 10/2009 | Powell | |
| 2009/0315684 A1 | 12/2009 | Sacco et al. | |

* cited by examiner

*Fig. 2 (Prior Art)*

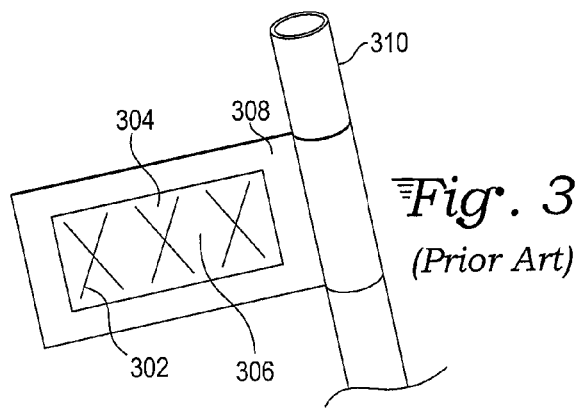
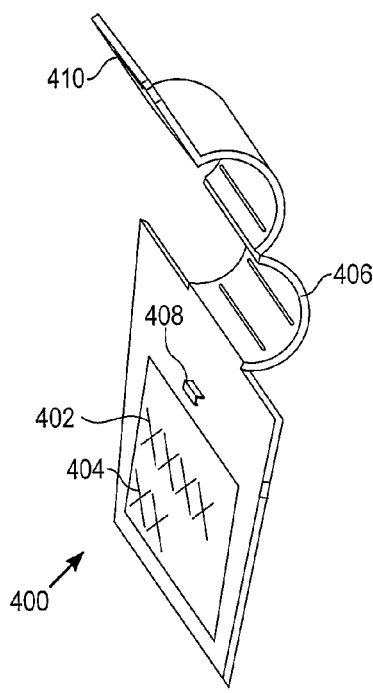
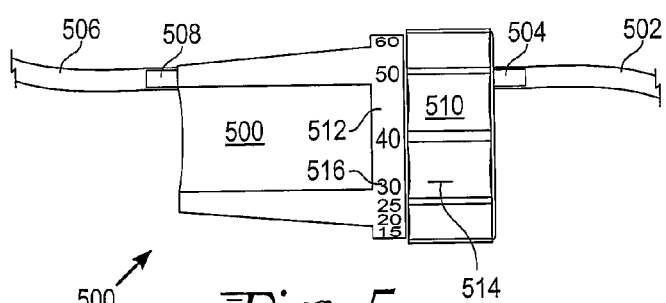
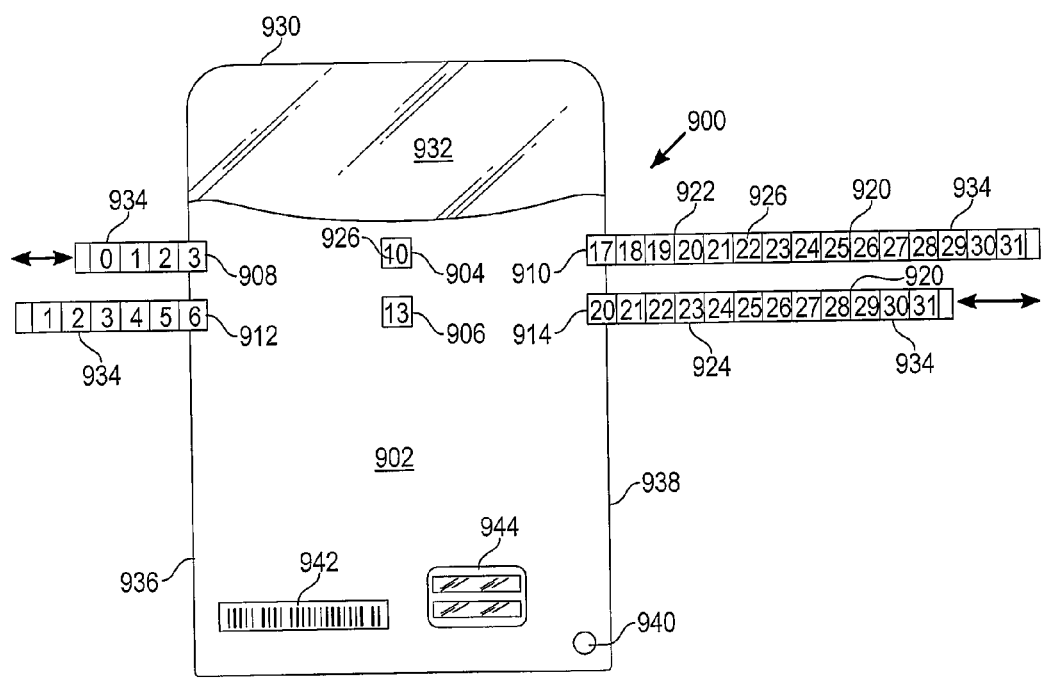

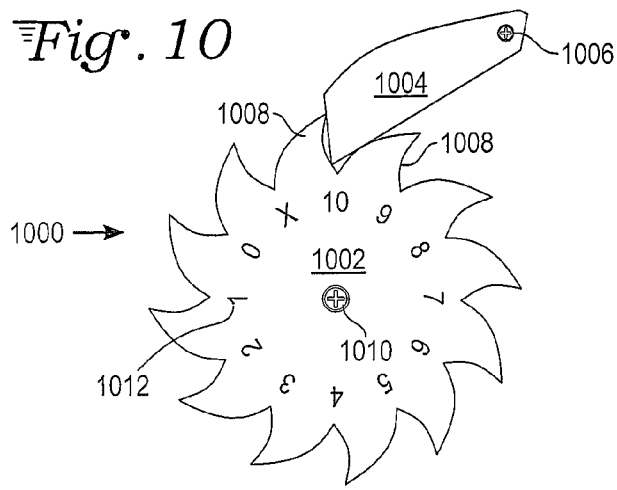
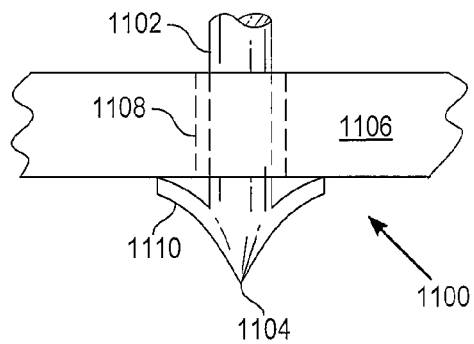
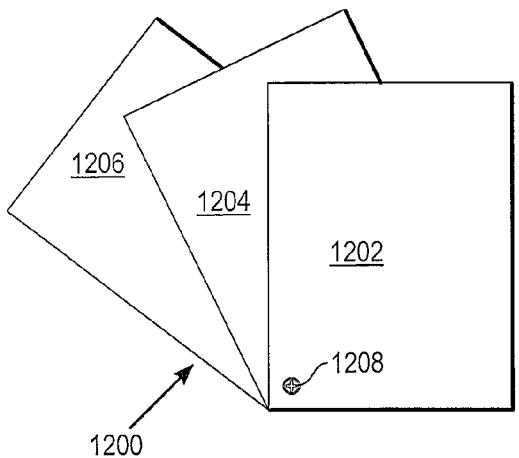
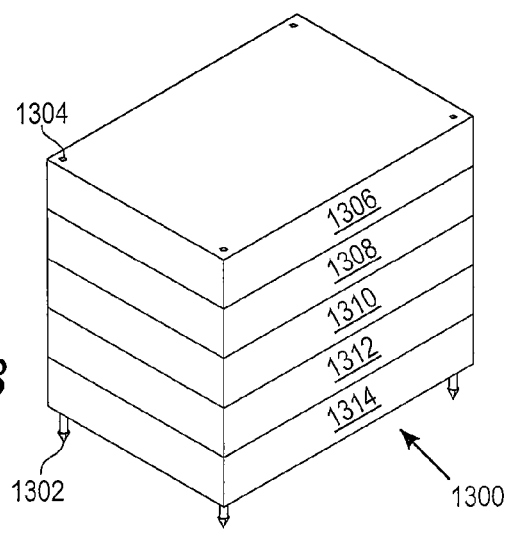

ically attached to
equipment can indicate recent usage, measurement, maintenance carried out or needed, notification of treatment, notification for product change out dates due to expirations or an indication of product, procedure or treatment completed. Such information can get communicated across shift changes and among personnel without direct person to person contact, and is less likely to be overlooked than when the information resides in a computer, on a clipboard, chart or other location physically separate from the equipment.

MANUALLY SETTABLE TAMPER RESISTANT INDICATOR DEVICE

CROSS-REFERENCE TO RELATED APPLICATION

This application claims priority from U.S. Provisional Application Ser. No. 61/244,818, filed Sep. 22, 2009.

TECHNICAL FIELD

The field of the present invention relates generally to indicators and more specifically to lockable, settable indicators of a manually operated type.

BACKGROUND

In medical and other professions and industries, it is well known to attach a handwritten message to equipment in order to indicate status, maintenance or replacement needs related to the equipment. Transparent or opaque tape can attach a piece of paper to equipment. Adhesive labels can be adhered to equipment. Tags can be attached with strings, zip ties, straps or tape. With a pen, marker or pencil, information is written on a paper or writable plastic surface of the tag or label, or directly on dressings, medication vials, medical devices and containers.

While information may be entered into computer systems, having a durable record of current information attached to a respective piece of equipment can provide direct and throughput communication. This is especially vital in the medical profession, where information physically, visibly attached to equipment can indicate recent usage, measurement, maintenance carried out or needed, notification of treatment, notification for product change out dates due to expirations or an indication of product, procedure or treatment completed. Such information can get communicated across shift changes and among personnel without direct person to person contact, and is less likely to be overlooked than when the information resides in a computer, on a clipboard, chart or other location physically separate from the equipment.

Medical providers utilize medical devices for therapies and treatments, many of which have a primary and secondary expiration date. Many devices, products, apparatuses, tools, instruments, pieces of equipment, compounds, fluids, foods, fats, medications, and the like have a viable lifetime with an expiration date depending how they are used. Other industries may have devices and substances with single or multiple expiration dates. When these devices are used over time, or used after the viable lifetime or the expiration date, the risks of complications multiply and/or the product begins to degrade; therefore the device must be replaced or changed out. Germs begin proliferating after time and the device must be changed out to reduce risks and complications related to infection control. Other risks in the hospital or healthcare setting include hospital acquired infections, blood clots, blood stream infections, dressing infections, air embolism, and poor device or product performance. Therefore, it is desired or required to change out materials or provide maintenance once a specified usage time has elapsed.

There is a great need for implementing measures to ensure compliance to change out intervals, thereby reducing risks of infection and complications. Yet, as a result of shortages of nursing and healthcare providers of different disciplines and pressures for hospitals to make profits, infection control measures and methods of delivering care have been found to be inconsistent. Compliance audits performed by facilities have also shown infection control and product safety compliance are inconsistent. Hospital acquired infections have increased in clinical settings. Preventable events such as contaminated drugs or devices, incompatible blood transfusions, air embolism, decubitus, certain hospital acquired infections including urinary tract infections, hospital acquired pneumonia, bloodstream infections, surgical site infections, insertion site infections, wrong preparation of medications, patient death or serious disability associated with the use or function of a device in a patient's care in which the device is used for functions or in a manner other than intended, any incident in which a line designated for oxygen or other gas to be delivered is contaminated by toxic substances, or a line is crossed over to another device with similar attaching ports, would be greatly decreased if critical information could be communicated more reliably on site.

Other industries and professions benefit from communication of critical information on site. For example, electrical and power cords are often difficult to identify as to which power source goes with which device. Electrical lines from power boxes often need to be retraced to determine the identity of the line. Safety, efficiency and ease of use of equipment can be improved with direct, visible communication of information relating to the equipment.

SUMMARY

A manually settable, tamper resistant indicator device is suitable for use in medical and other professions. Setting indicated information on the device and attaching the device to a piece of equipment or a product allows the information relevant to the equipment or product to be displayed in a manner that may reduce error or waste, especially in a medical environment.

A method is disclosed for visibly indicating information on the medical device attached to a medical patient. The indicator device is sterilized. The indicator device is affixed to a medical device. The medical device is attached to a medical patient. The indicator device is set to display information relating to the medical device. Such information includes a day, a date, a usage count or a personnel identifier. The indicator device is set to display the information concomitantly with attaching the medical device to the medical patient.

The displayed information is locked by fixing an indicia member of the indicator device relative to the pointer member of the indicator device. The locking is performed in a tamper resistant manner. Setting the indicator device includes manually moving at least a portion of the indicia member relative to at least a portion of the pointer member.

An indicator device is disclosed, and is suitable for use in the disclosed medically related method and in other professions and environments. The indicator device has a plurality of sliding strips having indicia thereupon. A pointer member has at least one pointing area.

A tamper resistant locking member is operable to fix at least a portion of the indicia member to at least a portion of the pointer member. The indicator device includes a fastening device. Each sliding strip is mounted to the pointer member. Each sliding strip is independently manually movable to display a respective selected one of the indicia at the pointing area.

BRIEF DESCRIPTION OF THE DRAWINGS

FIG. 2 is an elevated view of prior art adhesive labels for medical use.

FIG. 3 is a perspective view of a prior art printed or handwritten label laminated and attached with transparent tape to medical tubing.

FIG. 4 is a perspective view of a prior art clip on tag.

FIG. 5 is a perspective view of a prior art in-line settable flow rate valve.

FIG. 9 is a perspective view of a variation of the manually settable indicator device of FIG. 1, having at a least one sliding strip with indicia.

FIG. 10 is an elevated view of a ratchet mechanism usable in the indicator device of FIG. 1, 7 or 9.

FIG. 11 is a side view of a lockable pin inserted into an aperture, suitable to the indicator device of FIG. 1 or variations.

FIG. 12 is an elevated view of a fan arrangement mechanism in a fan out mode, suitable to the indicator device of FIG. 1 or variations.

FIG. 13 is a perspective view of a stacking arrangement of indicator devices or portions of an indicator device, suitable to the indicator device of FIG. 1 or variations.

DETAILED DESCRIPTION

Figure 1:
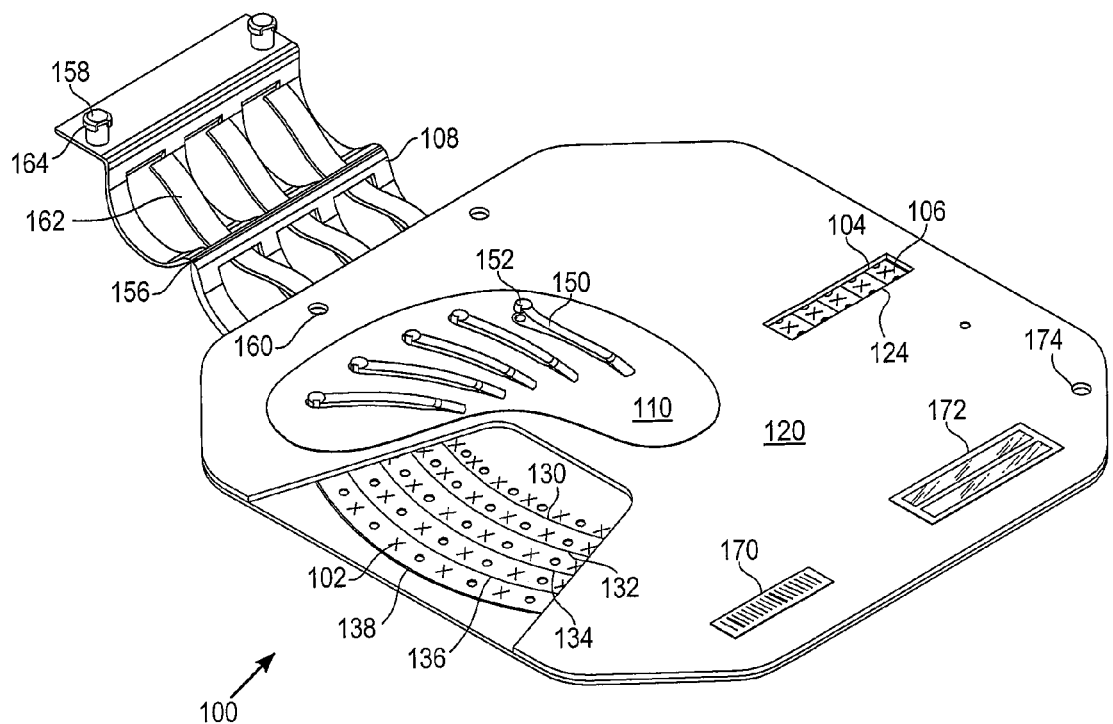
FIG. 1 is a perspective view of a manually settable indicator device in accordance with the present invention, having at least one flat disc with indicia.

With reference to FIG. 1, a tamper resistant, manually settable indicator device 100 in accordance with the present invention is shown. The indicator device features indicia 102, a pointer 104 to a selected one of the indicia 106, and a mechanism 110 that resists tampering with a setting of the selected one of the indicia relative to the pointer. Tamper resistant is herein defined as offering resistance or opposition to attempts to corrupt, interfere with, manipulate or alter a structure or the contents or settings of the structure. A tamper resistant feature reduces the likelihood that data is deliberately or accidentally altered, and makes the data lockable.

Suitable for use in medical and other professions, this indicator device 100 assists health care providers and others in compliance with safe practices, such as documentation of starting or expiration dates of products, or other pertinent data. A further suitable use is in retail clothing, to lock in a sales price or prevent switch out of price tags and altering of data. The indicator device ensures accuracy of documentation of the date of the expiration or start of usage in order to encourage proper change out or adherence to a maintenance schedule. Information is mechanically entered and represented in the device, before or after fastening the indicator device to a replaceable or disposable medical device. A tamper resistant locking feature mechanically prevents changing of the data. Information cannot be lost due to low batteries or electronic system glitches, as the indicator device 100 is mechanical. The device provides a visual reminder of when equipment to which it has been attached requires changing, disposal or service.

A fastener 108, included with the indicator device 100, attaches the device to a product or a piece of equipment. When operating the indicator device, a user sets a selected one of the indicia 106 relative to the pointer 104, applies the tamper resistant mechanism 110 to fix the setting of indicia, and attaches the indicator device to the product or piece of equipment. In this tamper resistant manner, the indicator device is set to display an indication, such as a start, expiration or service date or time or other information relating to the product or piece of equipment to which the indicator device is attached. In a medical setting, the displayed information may include a starting day or date, an expiration day or date, a usage count such as the number of times a device has been used or the number of times remaining for the device to be used, or a personnel identifier or other relevant information.

Examples of the indicator device have various types of indicia, pointers, mechanisms for setting the indicia relative to the pointer, tamper resistant mechanisms, fasteners, some of which are tamper resistant, form factors and other aspects, as will be discussed below. Compared to known methods and mechanisms for recording, indicating and displaying crucial information relating to a product or piece of equipment, especially in the medical profession, the indicator device may reduce error, lost information, deliberate or accidental changing of displayed information, wasted time in determining or retrieving correct information, and other hazards.

Figure 2:
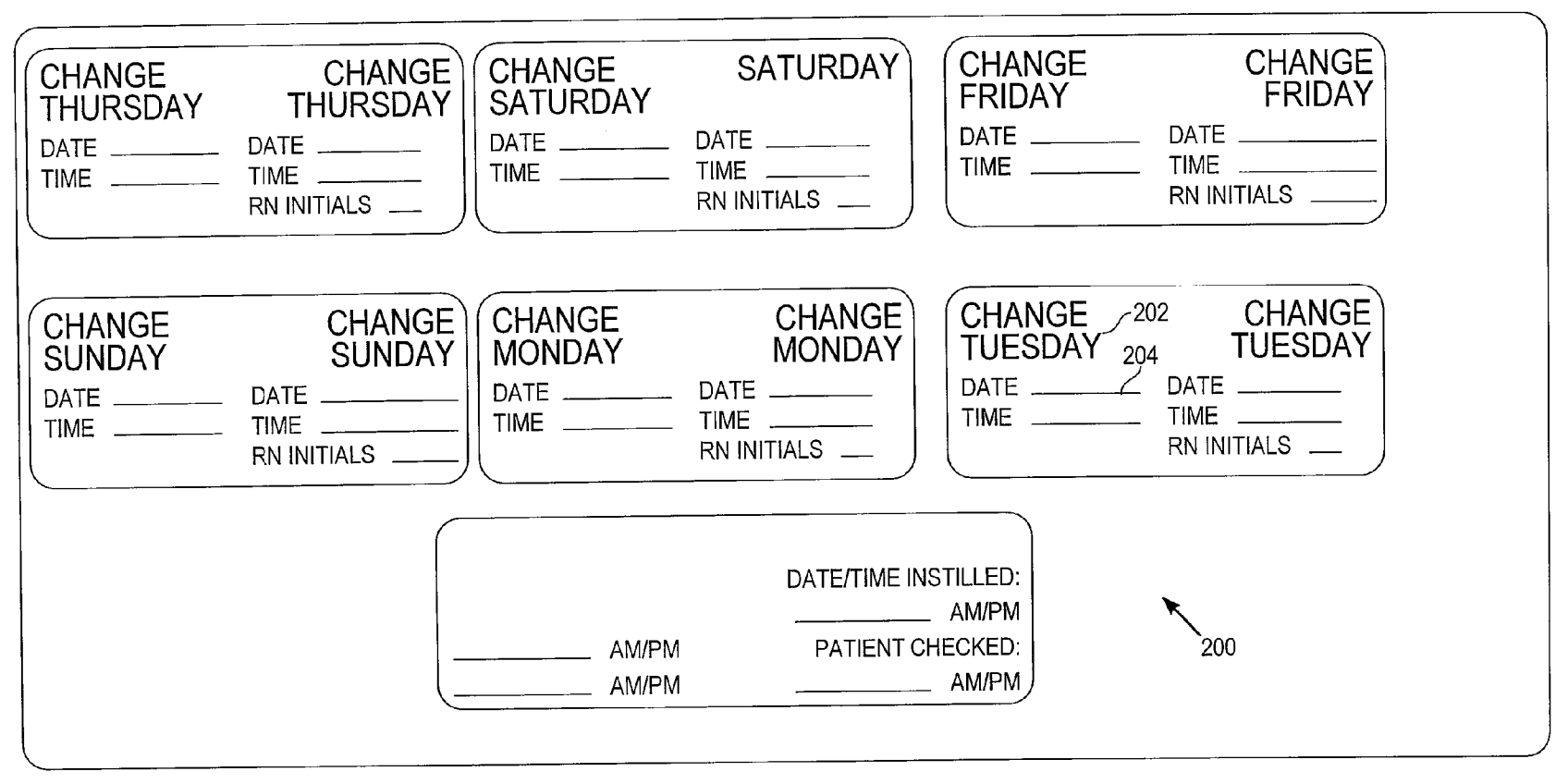

With reference to FIG. 2, adhesive labels 200 with a combination of printed 202 and handwritten information 204 are known and used in medical and other professions. Labels may be color-coded for day of the week and may be rectangular, adhesive backed paper with a writable surface and space to write a date, a time and the initials of a Registered Nurse or other medical professional. Medical providers or institutions have long relied on different methods of tracking expiration dates by the use of stickers with an expiration date as a type of identification. Medical personnel manually write the date of expiration or the date of implementation on the sticker or the device itself, or directly on a dressing. Traditionally, a label is adhered to a disposable medical device by an attending nurse or other medical personnel, and a note with a start or expiration time and day or date is handwritten on the label. The note and label inform medical personnel on subsequent shifts in different locations of when to dispose of or replace the medical device or medication. On or prior to the expiration date and time, the disposable medical equipment must be removed and safely disposed of, or maintained or replaced if the need for the equipment is ongoing.

Although labels are inexpensive and easily used, they are problematic. Information written with a pen, marker or pencil by one person may be illegible to another person, opening up possibilities for error that may be anywhere from annoying or wasteful to damaging or even fatal. Displayed information may be crossed out or scribbled over, giving rise to doubt as to which information is correct. Bacteria and cross contaminations are known risks of methods using writing with a pen or marker in a hospital, health care facility or other medical environment. Even if the sticker is sterile, the pen or marker may not be so. Use of an unsterilized pen, marker or pencil may transfer a pathogen to equipment and thence to a patient. Documentation written on a patient's chart may not accurately reflect status of the medical equipment used in procedures, as an insertion or start date may not have been entered into the chart. A label may fall off of the equipment or otherwise be misplaced, possibly being replaced on the wrong equipment. The process of writing the note and adhering the label to the medical device is nonsterile, time-consuming and error-prone as well as open to tampering.

With reference to FIG. 3, use of a paper label 302 with printed 304 and/or handwritten information 306, attached with transparent tape 308 to a piece of disposable tubing 310 or other equipment, is known. The transparent tape laminates the label, preventing alteration to the information that was written on the label before the tape was applied. Attempts to peel the tape off of the label will usually tear the label or the tape and provide a visual cue that a tampering with the label has occurred. Although the label attached and laminated with transparent tape is somewhat tamper resistant, contamination and other concerns nonetheless apply. Carrying around a roll of tape or tape and a dispenser is both inconvenient and unsanitary. Use of handwritten information on the label, prior to lamination, has similar problems to the exposed labels above, except the lamination protects the label from being overwritten.

With reference to FIG. 4, a snap on or clip on tag 400 is known, and may contain a combination of printed 402 and handwritten information 404 as with labels. An integral clamp 406 snaps around tubing or other receiving area on a product or piece of equipment, so that the tag displays the relevant information at the location of the product or equipment. A prong 408 at one end of the foldable clamp engages a hole 410 adjacent to the other end of the clamp 406, fastening the clamp closed. However, the clamp is reusable and is thus easily removed from the tubing, which can give rise to errors. The use of handwritten information on the tag has the same drawbacks as with labels above.

With reference to FIG. 5, a settable in-line IV flow regulator valve 500 is known in the medical profession, as used for intravenously administering fluid medicine at a controlled flow rate. Before or after connecting tubing 502 to an inlet 504 of the valve and tubing 506 to an outlet 508 of the valve 500, a medical practitioner rotates or twists one segment 510 of the valve relative to another, numbered segment 512 of the valve to set a flow rate. A line segment 514 on the rotatable section 510 aligns with or near a number 516 on the numbered section 512, to indicate the flow rate setting. There is no lock or other tamper resistant mechanism on the setting, as the setting is changeable. Although information is settable on the in-line IV flow regulator valve, the information relates solely to the setting of the valve itself and does not communicate a start date, change out date, expiration date or other information related to equipment to which the valve is attached.

In contrast to methods requiring handwritten documentation, use of the manually settable indicator device of FIG. 1 can be accomplished without the use of a pen or a marker. The indicator device can be packaged in a sterile condition in sterile packaging, for single use and disposal along with an expired medical device. Since the indicator device is lockable, a tamper resistant proof of e.g. date of insertion, start date or date of expiration is on the medical product itself, which will increase compliance and reduce workarounds or shortcuts. Since the indicator device provides a visible reminder, excess waste from throwing away medical products with an uncertain history is reduced. Healthcare needs relative to disposable medical devices are readily determined when a patient is transferred from unit to unit, with a glance at the indicator device and without need to consult a chart or electronic record. This saves time and reduces error and waste.

Figure 6:
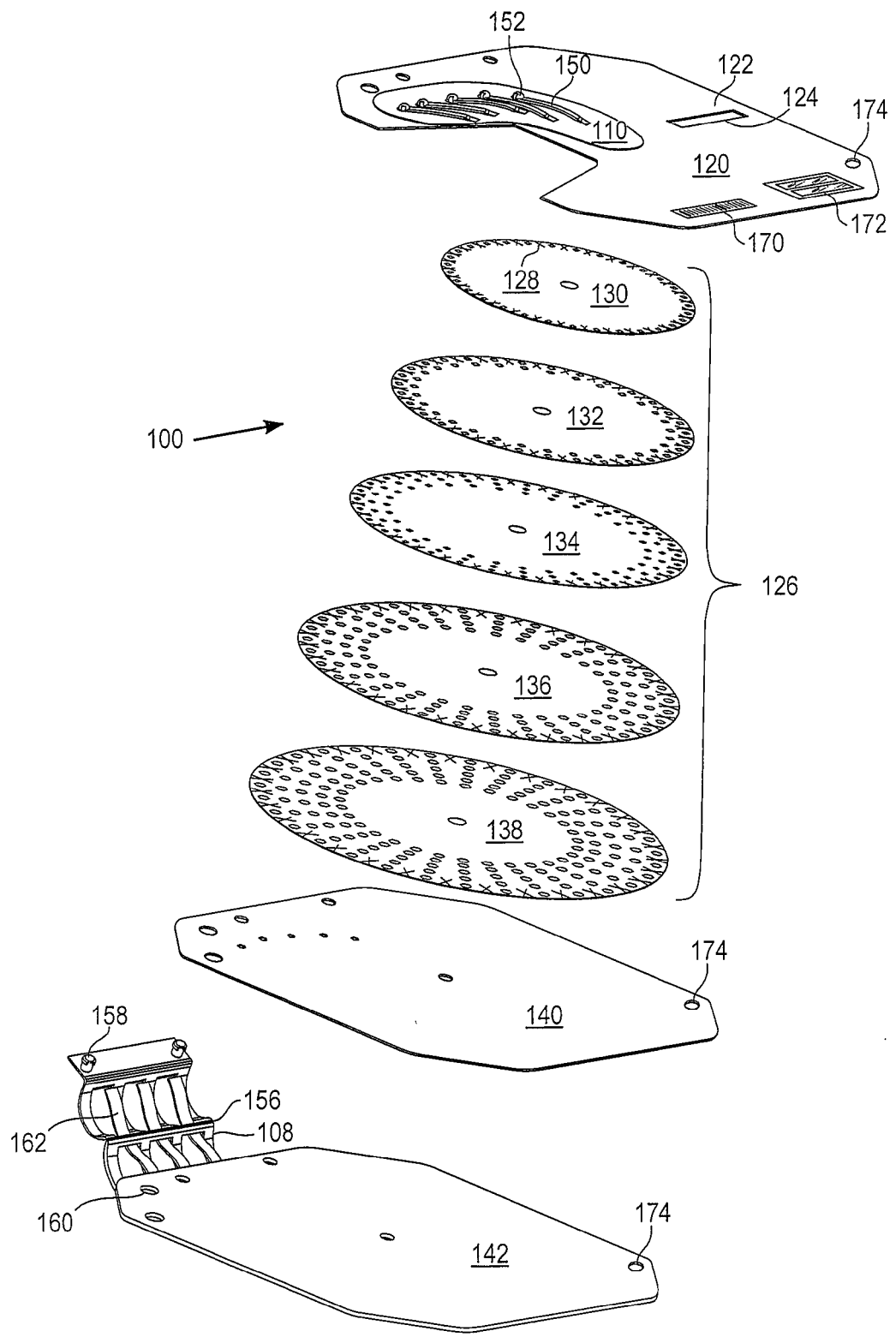
FIG. 6 is a perspective exploded view of the manually settable indicator device of FIG. 1.

With reference to FIG. 6, included members of the example of the indicator device 100 of FIG. 1 are shown in an exploded view. A first member is a pointer member 120, and has a pointer 122 with a window 124 to indicate the settable information. Further examples of the indicator device have other mechanisms on the pointer member for indicating settable information, which may include a plurality of windows, a window being an aperture, a window being a transparent section, an index marking, a line segment, an arrow or other pointing symbol, text, numbers, stampings, embossing, ridges, other raised, lowered or otherwise distinguishing features as a pointing area or combinations thereof. A second member is an indicia member 126, and has indicia 128 such as symbols, alphanumeric characters separately or in groups as text, colors e.g. from a color code or other markings as known in the art. Indicia can include days of the week, months, dates, hours or minutes as may relate to starting or expiration times, words, abbreviations, numbers, individual or grouped characters or symbols or other information, units of measure or even pricing or other product information. Further, indicia can include a letter from the alphabet, one or more barcodes, a watermark, a location, and operator identification, a picture, a drawing, a photograph or other representation. In one example, baseline information pertaining to a patient, such as a measurement of a circumference of a patient's arm, a volume of a fluid output or how many times a device associated with the patient has been exposed to CT (computerized tomography) or sterilization and so on, is settable on the indicator device using the indicia. Indicia can be printed or drawn or otherwise reproduced in a single color, in multiple colors, or in glow-in-the-dark ink or other material. The indicia are alignable with the window 124, line segment, arrow, pointing symbol or other pointing area.

The first 120 and second 126 members are retained together, as the first member 120 may retain the second member 126, the second member may retain the first member or the first and second members may be retained by another portion of the device. The first member and the second member cooperate in at least two types of settings. In a temporary or unlocked setting, the first member and the second member are manipulable, and the setting of the indicated one of the indicia may be changed readily. In a locked setting, one of the indicia is aligned with a pointer, and the indicator device resists a manipulation of the first member and the second member relative to each other. The locked setting may be permanent, with breakage or damage to the locking mechanism upon any attempt to unlock the indicator device. In a variation, the locked setting may be unlocked with a key and resist unlocking without a key. In a further variation, a partially locked setting allows manipulation of a portion of the first member or the second member, with a further portion of the first or second member being locked.

In the example of FIGS. 1 and 6, the indicia member 126 includes a plurality of discs 130, 132, 134, 136 and 138, each disc having indicia. The discs are rotatably attached or mounted to the pointer member 120, so that each disc may be rotated independently of the others, and indicated information from each disc may be set independently of the other discs. The discs may be mounted concentrically, as in FIG. 1, or in other arrangements such as with each disc having a rotation mount and window or other pointer separate from rotation mounts and pointers of the other discs. A base plate 140 and/or a backing plate 142 may be used as part of a mounting. In a variation, an RFID tag 172, a barcode 170 or other identification device may be attached to the pointer member 120, the base plate 140, the backing plate 142 or elsewhere on the indicator device 100 for purposes of identifying the indicator device or the object to which the device is attached.

A tamper resistant third member 110 is included in the indicator device of FIGS. 1 and 6. Tamper resistance is brought about by a relative ease of assembly and resistance to disassembly. A tamper resistant part may include the likelihood of damage to the part or to a companion piece during disassembly. In the example, the tamper resistant member 110 includes a flexible arm 150 extending from or otherwise attached to the pointer member 120 and having a pin 152 or tab with a one-way head. The one-way pin 152 or tab is inserted into an aperture in the indicia member, and resists or opposes being removed from the indicia member. Resistance to removal is provided by the one-way head, which may have an arrowhead or hook shape easily inserted but difficult to remove. Insertion of the one-way pin or tab locks the indicia member relative to the pointer member, fixing the indicated one of the indicia in a tamper resistant manner. Such a one-way pin or tab, or pin or tab with a one-way head, is a type of locking pin or locking tab. Where a plurality of discs is included in the indicia member, a locking pin may lock all of the discs as by inserting through a respective hole in each respective disc, or each disc may have a respective locking pin and corresponding hole in the disc as shown in FIG. 1, or other combinations of locking pins, locking tabs, locking discs or other tamper resistant members may be applied. A locking pin may insert to a hole in the indicia member and continue on through a further hole in the pointer member, similarly resisting or opposing being removed. Partial locking may be accomplished by having one pin lock to one disc, while another pin is not locked to another disc. In a variation, first and second portions of the indicia member or the pointer member are independently lockable.

In a variation, a flexible arm extends from the indicia member, and has a pin that inserts into and locks to the pointer member. Thus, the locked setting includes a third member attached to the indicator device and locking to the first member, the second member or both. In the locked setting, the third member resists unlocking from the first member or the second member. Thus, the tamper resistant member is attached to at least one of the pointer member and the indicia member. The tamper resistant member is securable to at least one of the pointer member and the indicia member, and opposes removal from such a member once so secured, so that a relative positioning of the pointer member and the indicia member is fixed.

A fastening device is included in the indicator device 100 of FIGS. 1 and 6. In the example, the fastener is a clamp 108 dimensioned to fit around and clamp to tubing such as found in certain types of medical equipment. The clamp may be a single piece molded along with the pointer member and having a living hinge 156. The clamp may be dimensioned to secure the pointer member and the indicia member to a section of tubing or a disposable medical device. A tamper resistant version of the clamp has a locking pin 158 or locking tab, using a one-way head 164 that inserts into an aperture 160 such as a hole or a slot in a mounting area or other portion of the indicator device 100 and resists disassembly or removal. The one-way head 164 may have beveled or flexing angled prongs, an arrow head cross-section or other shape or cross-section known in the art. Fingers 162 may be integrally molded with the clamp, and the fingers grasp the tubing when the clamp is closed, holding the clamp in place and preventing the clamp from easily sliding up and down along the tubing.

Other types of fasteners may be included with an indicator device. Examples of such fasteners are an integral zip tie, an adhesive surface e.g. a backside of the indicator device, a string that can be tied in a bow or a knot, a strap and twist ties. Various closures may be applied to a strap such as snap closure, hook and loop, one-way closure as on a zip tie and other mechanisms known in the art. A fastener may be formed as an integral part of the indicator device, for example a strap molded as part of the pointer member, or the fastener may insert through an aperture 174 of the indicator device 100 or otherwise fasten to the indicator device. A fastener may include a coupling or fitting that is complementary to or otherwise compatible with a coupling or fitting on a product to which the indicator device is to be attached. A fastener may splice the indicator device into another product, cuff around, clip onto, be threaded onto, slide into a groove in, insert and expand for a friction fit into, snap on to, assemble in two halves onto, or stack with portions of a product and so on. Splicing may be accomplished, for example, by attaching the cut ends of a tube or open ends of two tubes to flowthrough fittings such as nipples on adjacent or opposing sides of the indicator device. Splicing means are depicted in the known in-line IV flow regulator 500 as shown in FIG. 5. Some fasteners provide tamper resistance, as with a zip tie or one-way closure strap having a one-way cinch or other one-way closure which may be fastened readily but resists or opposes removal. A fastener which is not easily removed, but may be cut off, is not reusable and is thus tamper resistant. Tamper resistance may be provided by either or both of lack of reusability of a damaged fastener or visible indication of tampering as a result of damage to the fastener from removal or attempts at removal.

Embedding an indicator device into a product provides resistance to removal. The indicator device may be fused into a product after a first stage of product manufacture, molded with a product during manufacture of the product, manufactured separately and later assembled into a product or otherwise sealed or joined with a product so as to preclude removal of the indicator device from the product except through extensive damage to one or both of the indicator device and the product. Such visible damage provides both a deterrent to removal of the indicator device or components thereof and evidence of tampering when removal is attempted or has occurred.

Figure 7A:
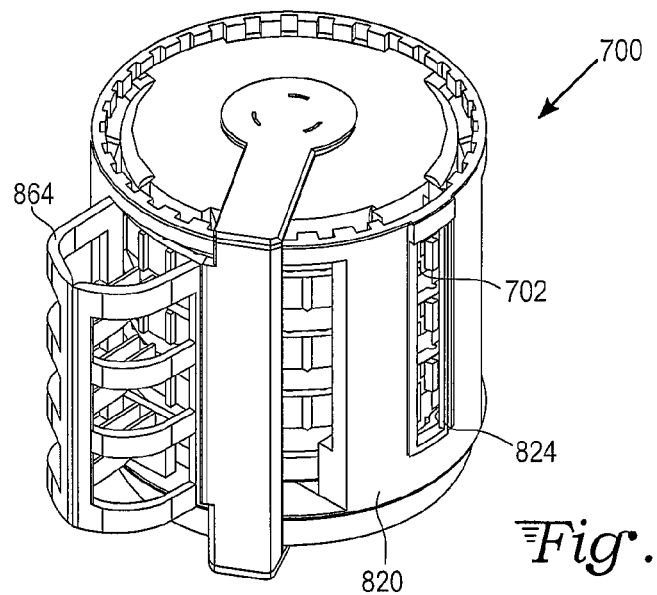
FIGS. 7A and 7B show a perspective view of a variation of the manually settable indicator device of FIG. 1, having at least one ring with indicia.
Figure 7B:
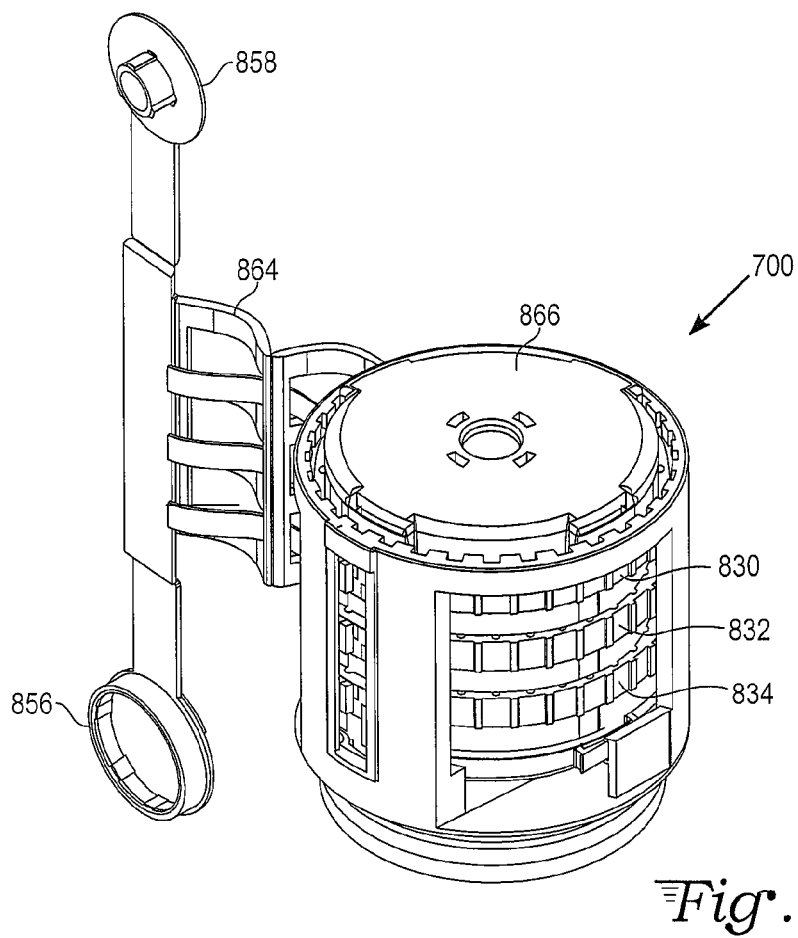
Figure 8:
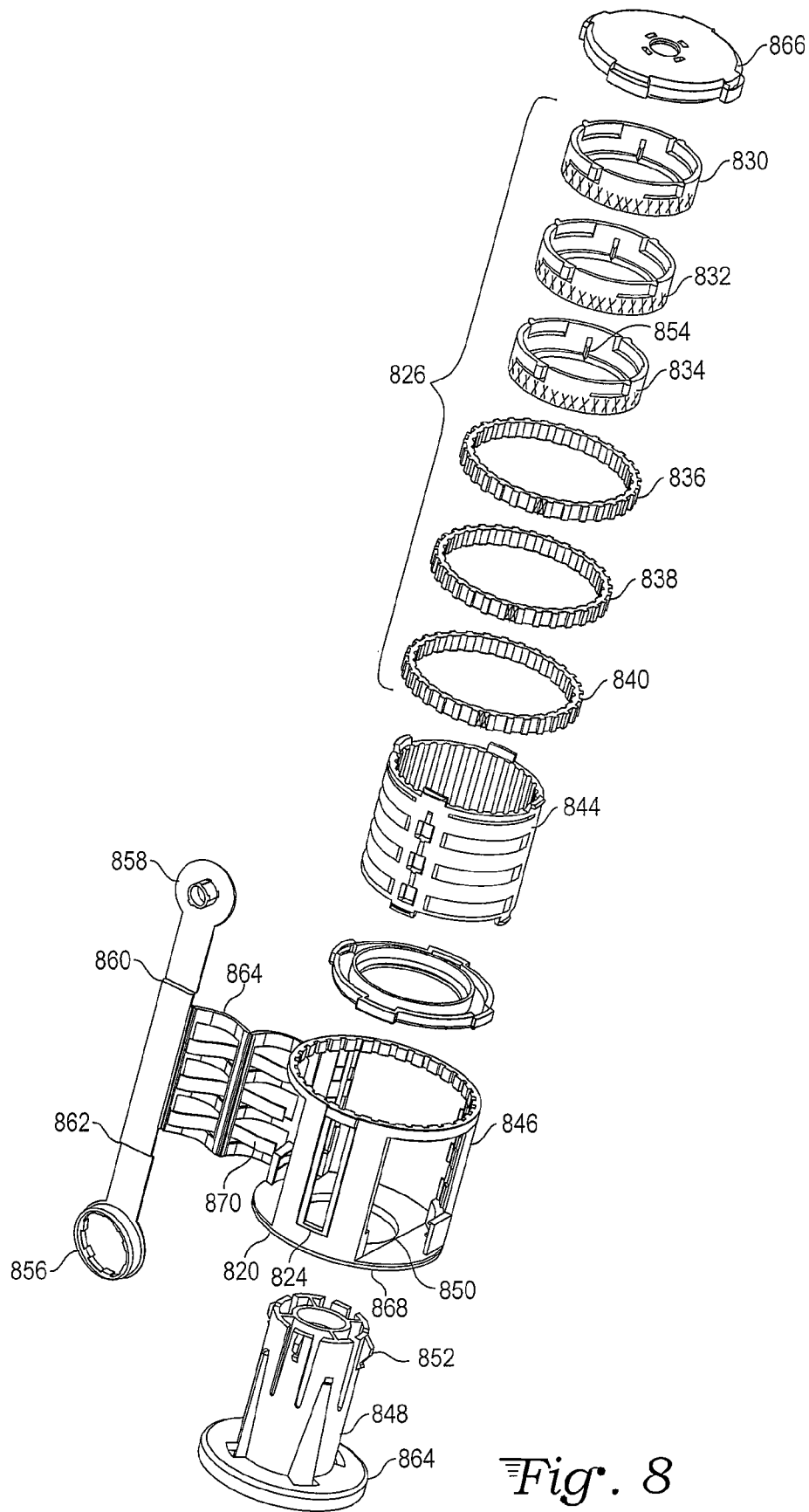
FIG. 8 is a perspective exploded view of the manually settable indicator device of FIG. 7.

With reference to FIGS. 7A, 7B and 8, a variation of the indicator device 100 is shown as the indicator device 700 having a generally cylindrical shape, although other shapes could be used. A pointer member 820 has a pointer 822 with at least one window 824 through which a selected one of the indicia is visible, and forms a cage or housing for the indicia member 826. The indicia member has at least one ring rotatably mounted to and within the pointer member. In the example indicator device 700, a plurality of rings 830, 832, 834, 836, 838 and 840, each having indicia, is rotatably attached or mounted within the pointer member. Each ring is individually rotatable and settable so that a selected individual or set of characters or symbols is visible through a respective window of the pointer member 820. Rings may have nubs or nibs, with the indicia member or the housing having corresponding ribs, detents, spring loaded or levered members, giving tactile feedback and position retention to the rings. Rings may be of differing diameters, and mounted in different sections of a housing or of the indicia member, as with inner and outer rings, upper and lower rings, staggered rings or various sets of rings. Various combinations of cages, such as an inner 844 cage and an outer cage 846, may be used in housings with different types or sizes of rings. Each ring may be manually rotatable and settable, or a key may be used to rotate and set each ring. In one example, outer rings 836, 838 and 840 are manually settable and inner rings 830, 832 and 834 are set with a key 848.

When used, the key 848 is inserted through an aperture 850 at one end of the housing, the pointer member 820 or the indicator device, until prongs 852 of the key 848 engage projections 854, grooves or slots on an inner surface of a ring of the indicia member. Rotating the key rotates the ring to which the key is engaged. Once a desired setting is achieved, with a selected one of the indicia 702 pointed to by the pointer member 820, the key is pressed further inward to the housing to engage another ring. The process of engaging, rotating and setting each ring is repeated, until all rings have been set. A final press of the key locks the key in place, preventing tampering with the settings of the rings. The key may have one or more one-way prongs, a one-way lip projecting inwardly or outwardly or other mechanism known in the art that fastens readily and resists removal, providing a tamper resistance. In a variation, the key 848 presses into place and a one-way cap 856 fastens into place, covering the key and preventing the key from being reused. A key or a cap having such a one-way mechanism as one or more one-way prongs or a one-way lip is at least a portion of a third, tamper resistant member of the indicator device. One or more caps e.g. a top cap 858 and a bottom cap 856 may be molded as part of a housing, each cap having a living hinge 860 and 862. In the example of FIGS. 7 and 8, two caps 856 and 858, a tube clamp 864 with a one-way clasp and the pointer member 820 are all molded together in a unitary body as a housing for the indicia member 826. Fingers 870 may also be molded in with the tube clamp 864. A key 848 with an integral end cap 864, and a separate end cap 866 are assembleable to opposing ends of the housing or the pointer member 820. The two caps 856 and 858 integral with the tube clamp 864 attach to the end cap 864 of the key 848 and the separate end cap 866 respectively, closing the tube clamp 864 and preventing the key 848 from being removed. In this manner, the two caps 856 and 858 integral with the tube clamp 864 act as both a one-way clasp for the tube clamp 864 and a tamper resistant closure retaining the key 848 and the separate end cap 866 so that a setting of the indicia member 826 relative to the pointer member 820 is fixed. Other operating sequences and mechanisms with or without caps may be devised.

A locking key or a locking cap 856 is a portion of a third, tamper resistant member. The locking key or the locking cap 856 may lock to the pointer member, or in a variation may lock to the indicia member. Such a cap 856 or a key is assembleable to a cap receiving area 868 on at least one of the pointer member and the indicia member. Similarly to the indicator device of FIGS. 1 and 6, in FIGS. 7 and 8 the third member locks to one of the first member or the second member in a locked setting, and resists unlocking from the first member or the second member, so that a relative positioning of the first, pointer member and the second, indicia member is fixed.

In a variation of the indicator device of FIGS. 7 and 8, rings with indicia and pointers are stacked to build an indicator device. Each ring locks with an adjacent ring, using one-way prongs or other locking engagements. In one example, each ring has hooked prongs that fit into apertures on the next ring. In a further example, each ring has alternating hooked prongs and apertures. The rings are initially separated, and are then assembled while locking into place the relative positioning of the indicia members and pointer members.

With reference to FIG. 9, a variation of the indicator device of FIGS. 1 and 6 is an indicator device 900 that has a flat, generally rectangular shape, although other shapes could be used. A first, pointer member 902, which may be made of paper, fabric, foil, plastic or other suitable material, has one or more windows 904 and 906, which may be centrally located. Each such window is flanked by slots 908, 910, 912 and 914, one slot on either side of the window. A second, indicia member 920 includes one sliding strip 922 and 924 for each window 904 and 906 respectively. Sliding strip 922 has indicia 926 and is threaded through one slot 908, passes behind the respective window 904, and is threaded out through the other slot 910. Sliding strip 924 is threaded through one slot 912, passes behind the respective window 906, and is threaded out through the other slot 914. The strip 922 slides back and forth, showing indicia through and alignable with the window 904. The strip 924 functions similarly, with respect to the window 906. Each strip is slidably mounted to the first member. A tamper resistant third member 930 includes a flap 932 attached to or formed integrally with the pointer member. The flap has adhesive and may have a transparent window. To set the indicator device, each strip is slid until a desired one of the indicia 926 aligns with a respective window 904 or other pointer of the pointer member 902. After the indicator device is set, the tamper resistant third member 930 is applied. An adhesive flap 932 is folded over and adhered to both the pointer member and the indicia member, thus fixing the pointer member relative to the indicia member and fixing the setting of the indicator device.

In one version of the example shown in FIG. 9, the ends 934 of the sliding strips 922 and 924 are folded backwards to a backside of the pointer member 902, and the adhesive flap 932 is folded backwards to the backside of the pointer member, and adhered to the ends of the sliding strips and to the backside of the pointer member. The sliding strips are no longer movable and are fixed in place by the adhesive flap on the backside of the pointer member, while the indicated information is visible through the window 904 on the front side of the pointer member. In a further version, the adhesive flap has a transparent section or may be entirely transparent, and is folded forward to the front side 934 of the pointer member. The adhesive flap adheres to the pointer member and to the portions of the sliding strips projecting from the respective slots on the front side of the pointer member, and may adhere to a portion of each sliding strip at a cutout or aperture window 904 of the pointer member. The indicated at least one of the indicia is visible through the transparent section of the adhesive flap. Excess lengths of the sliding strips may be folded or torn off at the edges or sides 936 and 938 of the indicator device 900.

Tamper resistance is provided in at least a twofold manner. The adhesive flap prevents deliberate or inadvertent changing of the position and indicated information of the sliding strip, and attempts to unseal the adhesive flap will tear the paper or distort the plastic of which the device is made, thus showing evidence of tampering. The adhesive flap is a portion of a third, tamper resistant member attached to the indicator device, adhering to or otherwise assembleable to and resisting a separation or removal from at least one of the first member or the second member.

In order to attach the indicator device 900 to a product or a piece of equipment, one of the previously discussed fastening devices may be used. For example, the backside of the pointer member 902 may have adhesive for attaching to a medical dressing, and the indicia are set to indicate a change out time for the medical dressing. A peel-away backing may accompany either or both of the adhesive flap or an adhesive backside. In a variation, an adhesive backside traps the excess lengths of the sliding strips between the back side and a surface to which the indicator device is adhered, performing both a locking function for the indicia member relative to the pointer member and a fastening function for attaching the device to a product. In a further variation, a hole 940 punched through the pointer member 902 or other portion of the indicator device 900 provides a passage through which a zip tie or other fastener may be passed in order to attach the indicator device to an object. Hydrophobic materials may be used where the indicator device 900 is intended to adhere to a dressing. A barcode 942, an RFID tag 944 or other identification device may be attached to the pointer member 902 or other surface of the indicator device 900, for purposes of identifying the indicator device or the object to which the device is attached. The RFID tag 944 may be hidden inside the device in a manner known in the art.

In a variation, the indicator device 900 of FIG. 9 is incorporated into a beverage holder such as a coffee cup sleeve. In a further variation, the indicator device 100 of FIG. 1 is incorporated into a beverage holder such as a coffee cup sleeve. An indication pertaining to the beverage, such as the name, customer number or other identification of the customer purchasing the beverage, the type of beverage, ingredients added to the beverage, a serving time of the beverage etc. may be set using the indicia and the pointer of the indicator device as described. Other indicator devices may be embedded or otherwise incorporated into other products in a related manner.

With reference to FIG. 10, an indicator device such as shown in FIG. 1, 7, 9, 14, 18, 19, 20, 27 or 28 or other variations may use a ratchet mechanism 1000 to count down days, hours, usage cycles or other parameters relating to equipment or a product. The ratchet mechanism 1000 has a rotatable ratchet wheel 1002 and a pawl 1004. Pivoting on a pawl axis 1006, the pawl 1004 may be spring loaded or otherwise biased to engage the teeth 1008 of the ratchet wheel 1002. Pivoting on a ratchet axis 1010, the ratchet wheel may be turned in one preferred direction only, e.g. counterclockwise in FIG. 10, in a manner known in the art. As the ratchet wheel 1002 is advanced by rotating in the preferred direction one tooth at a time, the pawl prevents reverse rotation. Indicia 1012 may be stepped past a pointer such as a window or pointing symbol (not shown). Indicia may be arranged to count down, count up, sequence through a series or otherwise progress as the ratchet wheel is advanced. Other ratcheting, countdown or count up mechanisms, or a ratchet stop at a final position may be devised by a person skilled in the art. Ratcheting, countdown or count up mechanisms may advance or increment by a press on a button or lever.

Compatible features from various versions may be swapped or combined in variations of the indicator device. For example, an adhesive flap may be used as the tamper resistant third member for a flat indicator device having rotatable discs, made of paper or plastic. The adhesive flap may adhere to exposed portions of the rotatable discs, such as at a graspable section of a disc, as well as to the pointer member. A cylindrical indicator device may combine rotatable discs at one or both ends with rotatable rings. One or more one-way pins may be used as the tamper resistant third member for a cylindrical indicator device with rings, each pin inserting through a corresponding aperture in a ring. A transparent, tamper resistant cap or lid may seal over a flat indicator device having either rotatable discs or sliding strips. A tamper resistant fastener may perform both the function of fastening to a piece of equipment and preventing manipulation of the setting of the indicator device.

Further variations of the indicator device may be devised by a person skilled in the art. An indicia member or a pointer member may form a main body of an indicator device. A pointer member, such as a pointer, clock hands, a windowed disc or windowed sliding strip may be attached to the indicia member and movable to set the device. The pointer member may be moved relative to the indicia member, to make a setting of the indicator device by pointing to an indicated one of the indicia.

Displacement or removal of material may be used to point to indicia. For example, a region adjacent to indication text may be depressed or elevated differentially from further similar regions, indicating e.g. a day. A region adjacent to or including an indication text may be displaced upwards or downwards relative to the remaining regions, which are planar. The displaced region indicates e.g. the expiration hour. A region adjacent to an indicator text may be removed, such as by pushing or punching out a small disk of material, leaving the remaining material in place. The text indicated by the absence of material corresponds to an expiration hour or day. A pointer area may slide in or out relative to indicia. The pointer member may include, as a portion of the pointer, text such as: use by, guaranteed by, sell by, initials of a person or other proper name.

One or more pins or pegs may be an indicator, as applied to an indicia member with snap together portions that lock as by a one-way mechanism. Embodiments may have dials, revolving columns or rows, stackable interlocking or interconnecting dials, columns or rows, or elements positioned parallel or at right or other angles. Shapes may be concave or convex, or have various angles or curves. Relative motion of the pointer member and indicia member may include free spin, glide, click spin and finger control surfaces and mechanisms or a key or combinations thereof. A portion of an indicia member may rove all around a shape or through a maze in order for data to be redisplayed before locking in. A portion of an indicia member may have a shape of a band or ribbon, and be an open or closed loop. A portion of an indicia member may roll in one or more directions and then be locked into place, showing a one of the indicia. Barcodes may be used as at least a portion of the indicia. Indicia may include month, day, year, hour, day of the week, color, symbols, numbers, size, price, location or other data. An indicia member may include cards that flip to designate a field, or a rotatable three-dimensional shape such as a die or other polyhedron offering multiple sides or surfaces having indicia. In a variation, one or more portions of an indicia member or a pointer member are placed in a semi-locked position to accommodate changing data.

With reference to FIG. 11, an example of a locking mechanism 1100 is shown. A locking pin 1102 is inserted into an aperture 1108 through a locking pin receiving area 1106. The locking pin 1102, which may have a circular, square, rectangular or other cross-section, has a one-way head 1104, which may have a pointed or a rounded tip. The one-way head 1104 has at least one barb 1110 or other projection, which may be angled to facilitate insertion of the one-way head 1104 into the aperture 1108. The barb 1110 may flex, or a portion of the aperture 1108 may yield, so that the one-way head 1104 is readily inserted into and through the aperture 1108 and is not readily removable from the aperture 1108. In this manner, the locking pin 1102 is locked into the locking pin receiving area 1106, resisting removal. Attempts to remove the locking pin 1102 from the locking pin receiving area 1106 may cause breakage of a portion of the locking pin 1102 or a tear or other visible damage to the locking pin receiving area 1106, providing visual evidence or indication tampering has occurred. Other shapes for a one-way head, an aperture, a barb or other projection or other types of locking pins may be devised by a person skilled in the art.

Locking mechanisms may include a primary lock or a secondary lock. Hooks may be used as locking mechanisms. A hook may slide, pivot or bend from one position to another, and a portion of a hook may enter a covered, enclosed, recessed or otherwise protected space that does not allow access to the hook. A slide in or slide out cover with a locking mechanism may be used. A case with a locking lid may be used. A portion of the device that crushes or is destroyed upon being locked and thereby prevents unlocking and reuse may be used. Twisting may cause internal parts to rotate into a position that does not allow further movement. Force from a spring or gas pressure may move a member into a locking position. Shrinkage or expansion of a protrusion or a recess may be employed in a locking mechanism. Complementary geometric shapes may engage or disengage in a locking mechanism. Adhesion of a portion of the device e.g. a tape, fabric, paper or plastic section, to itself or to another portion of the device may provide a measure of tamper resistance, as the tape or fabric may show alteration or tear if an attempt to tamper with the device is made. A pull string or wire may activate a locking mechanism, and the pull string or wire may detach upon activation. Squeezing a flexible portion of the device may activate an internal locking mechanism. Tumblers similar to those of a bicycle lock may activate a locking mechanism. Locking threads may be used for portions of an indicator device that twist together. A locking device may have a key to unlock or may be permanently lockable. Different types of keys may be used, such as a key for setting a dial or a ring, a key to lock or unlock a locking mechanism, or a setting key that also locks to a member.

Various materials, such as paper, plastics, glow-in-the-dark plastic, sponge, fabric, metal or metal foils, autoclavable or anti-microbial materials or coatings, may be used for portions or all of the indicator device. Hydrophilic or hydrophobic materials may be used, as to keep the device wet or dry respectively.

A method for operating the indicator device is described below. If the device is to be operated in a medical setting, it is assumed proper sterilization procedures are being followed. If applicable, the indicator device is removed from the sterile packaging. A desired setting of the indicator device is arranged by manually moving the indicia member relative to the pointer member, until the pointer member is proximate to and thus indicates or points to a desired marking that is one of the indicia. Relative movement of the indicia member and the pointer member is accomplished by rotating, sliding, or otherwise moving either the pointer member or the indicia member as appropriate to the mechanism of the indicator device. The desired one of the indicia is thus centered within a viewing window of the pointer member, or is pointed to by a pointing symbol or other indication of the pointer member. The setting process is repeated if needed for each independent component of the indicia member. A tamper resistant member of the indicator device is then applied to fix the relative positions of the pointer member and the indicia member, thus fixing the indicated one of the indicia and making the setting tamper resistant. The indicator device is fastened to a piece of equipment or a product to which the selected, indicated one of the indicia is relevant. The securing to a piece of equipment or a product may be done before or after the indicator device is set or fixed. Medical devices to which the indicator device may be attached include intravenous tubing, intravenous tubing valves, intravenous tubing ports, catheters, dressings, infusion equipment and supplies, drains, respiratory therapy devices and feeding tubes and others. A variation of the indicator device may be attached to a patient.

With reference to FIGS. 12 and 13, multiple indicator devices for an indicator device having multiple segments may be arrayed, displayed, combined or deployed in various arrangements. A fan arrangement mechanism 1200, shown in FIG. 12, deploys segments 1202, 1204 and 1206 of an indicator device, or entireties of indicator devices, in an extended fan-out position. Collapsing the fan arrangement, by moving each segment about the pivot point 1208 until all segments are aligned, allows for a compact or fan-in position. The pivot point 1208 may be at a corner of each of the segments, or at another location. A fan arrangement may be created by stacking two or more segments or entireties of an indicator device. One or more segments may be fanned in or out independently, or the segments fanned in or out in sequence.

A stacking arrangement mechanism 1300, shown in FIG. 13, deploys segments 1306, 1308, 1310, 1312 and 1314 of an indicator device, or entireties of indicator devices, in a vertical stack or alternatively in a horizontal stack. The stack may be created by inserting a pin such as pin 1302 of one segment of an indicator device into an aperture, such as aperture 1304 of a further indicator device. In the stacking arrangement 1300, the pin 1302 extends from a bottom most segment of the indicator device, and the aperture 1304 is presently on an upper most segment of the indicator device, available to receive a further pin from a further segment. Segments may have one or more pins, and the segments in the stacking arrangement mechanism 1300 are shown with four pins and four receiving apertures. The pins may be locking pins as in FIG. 11, or may be non-locking pins. In a variation, a single pin of a segment may be inserted into a single aperture of a subsequent segment, to form a fan arrangement as shown in FIG. 12.

Thus, an arrangement may be stacking or fanning, or both stacking and fanning. Stacking, fanning, extending or collapsing versions may be useful for updating information as a segment or an entirety of an indicator device passes an expiration date or time. The expired segment or device is superseded by a fresh segment or fresh device stacked on top of the expired one. An updated time, date or other indication may be set on the fresh segment or device.

FIGS. 14-22 show further variations of the indicator device of FIG. 1. The variations may have entirely mechanical operation, or may have added electronic devices or be usable with a tracking system as by having an included RFID or other electronically readable identifier device. Further variations may have sound, visual display, timers, light, read/write technology, a solar-powered battery or wireless circuitry or operation and/or a microchip.

Figure 14:
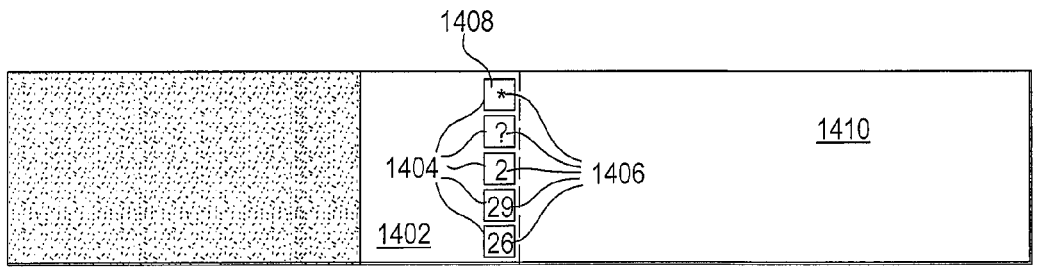
FIG. 14 is an elevated view of a variation of the manually settable indicator device of FIG. 9, having a pocket for one end of the sliding strip.
Figure 15:
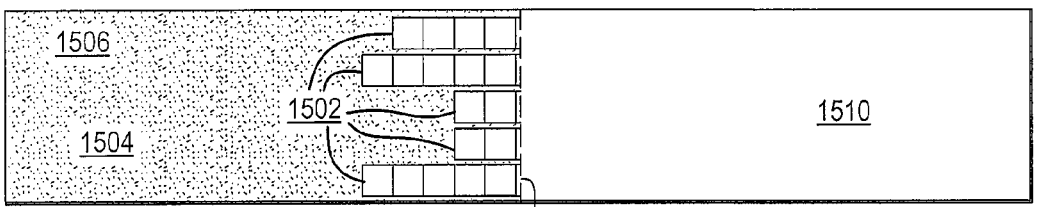
FIG. 15 is an elevated view of an opposing side of the indicator device of FIG. 14.

With reference to FIGS. 14 and 15, a variation of the indicator device 900 of FIG. 9 is an indicator device 1400 having a pointer member 1402 with at least one window 1404 or other pointer or pointing area, and an indicator member 1406 with a least one sliding strip 1502. A pocket 1410 or other structure having an interior region holds one end of each sliding strip 1502, an opposing end of each sliding strip 1502 being accessible externally from a backside 1504 of the indicator device 1400. The pocket 1410 may be formed by folding a flat material such as paper, plastic or metal foil, or assembling two flat rectangles, and adhering edges to form an envelope or other enclosure to contain the respective ends of the sliding strips, with the pocket being open at one end to allow the strips to slide and align with the pointer. Similarly to the indicator device 900, the strips slide past the one or more windows 1404, aligning a selected one of the indicia 1408 with each respective window 1404 to set the indication. An adhesive strip 1506 on the backside 1504 of the indicator device 1400 may have a peel off backing, and is folded and adhered to a portion 1510 of the backside 1504. The adhesive strip secures the free ends of the sliding strips 1502, fixing the setting of the indicia in a tamper-resistant manner. To assist in folding, a fold line 1508 may have markings such as a dashed line, or may be pre-creased or otherwise prepared in a manner known in the art. A backside of the pocket 1402 or envelope section or a backside of the section opposing the envelope section may have the adhesive backing.

Figure 16:
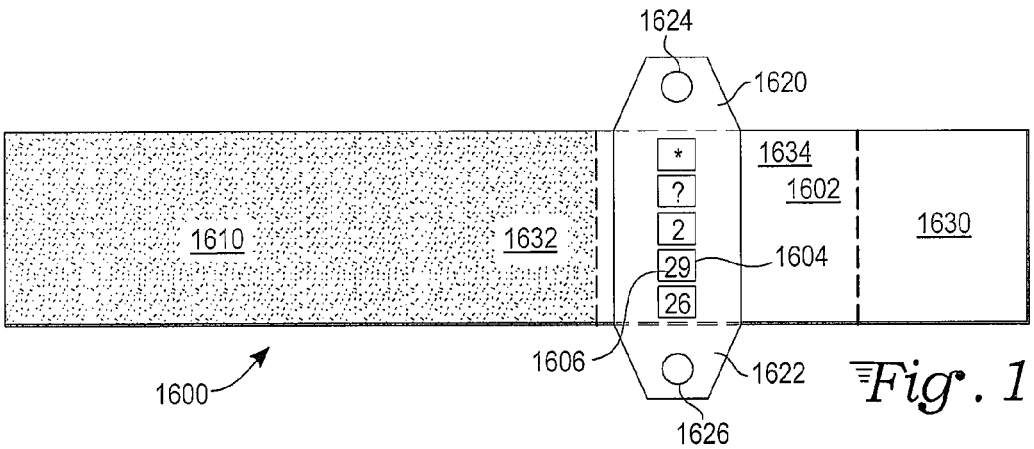
FIG. 16 is an elevated view of a variation of the manually settable indicator device of FIG. 14, having tabs and perforated sections.
Figure 17:
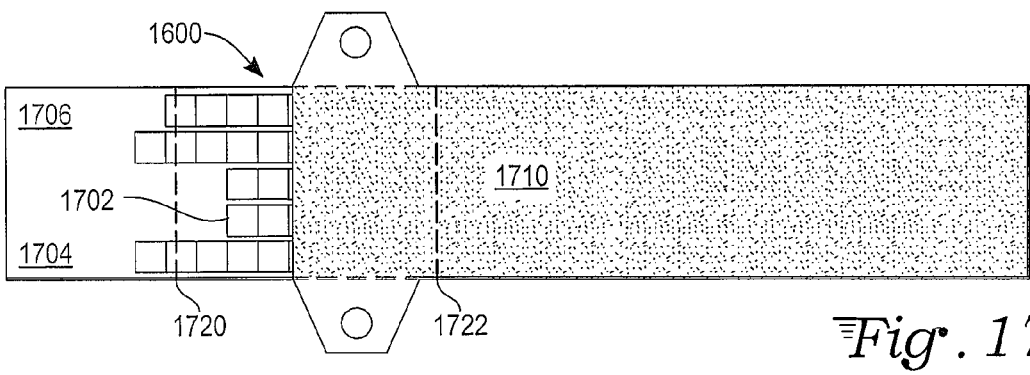
FIG. 17 is an elevated view of an opposing side of the indicator device of FIG. 16.

With reference to FIGS. 16 and 17 the indicator device 900 of FIG. 9 or the indicator device 1400 of FIGS. 14 and 15 has a variation as the indicator device 1600. A pointer member 1602 with at least one window 1604, an indicator member 1606 with a least one sliding strip 1702 and a pocket 1610 all have similar structure and function to the indicator device 900. One or more tabs of 1620 and 1622 attached to the indicator device 1600 function as a fastener, allowing the use of a twist tie, a zip tie, string or other portion of a fastener to be inserted through an aperture 1624 or 1626 of the tab 1620 or 1622 for fastening the indicator device 1600 to an article. Tubing may be inserted through aperture 1624 or 1626, thus fastening the indicator device 1600 to the tubing. An adhesive strip 1706 on the backside 1704 of the indicator device 1600 may have a peel off backing, and is folded and adhered to a portion 1710 of the backside 1704 and to the free ends of the sliding strips 1702. Perforations 1720 and 1722 allow a discard portion 1630 or 1632 of the indicator device to be torn off for disposal, leaving the remaining nonreusable portion 1634 of the indicator device with the setting secured in a tamper resistant manner. Generally, perforations in the indicia member or the pointer member are dimensioned so that a portion of the indicia member or the pointer member, respectively, is separable at the perforations.

Figure 18:
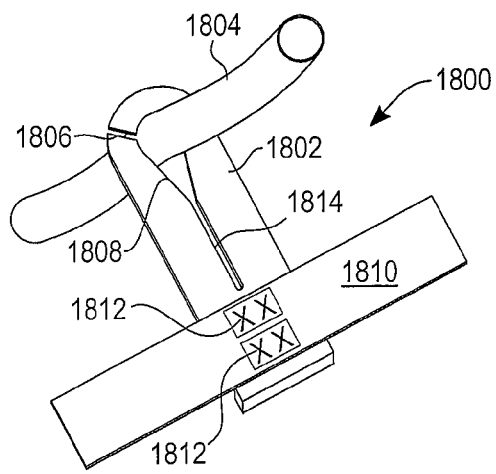
FIG. 18 is a perspective view of a further variation of the manually settable indicator device of FIG. 9, having a tube clamp.

With reference to FIG. 18, a tube clamp 1802 is a fastener for an indicator device 1800, as a variation of the indicator device 900 of FIG. 9. Structure and operation of the pointer member 1810 and indicia member 1812 are similar to those of the indicator device 900. A gap 1806 in the tube clamp 1802 opens to allow tubing 1804 to be inserted into an open region 1808 of the tube clamp 1802. Alternatively, the gap 1806 may be opened and the tube clamp pushed onto the tubing 1804. Depending upon whether the tubing 1804 is desired to be open and flowing a gas for a liquid, or pinched off and closed, the tube clamp 1802 is slid so that the tubing is in an open teardrop-shaped region 1808 or a pinch region 1814, respectively. The gap 1806 may be located as shown in FIG. 18 or elsewhere as may be devised, or the tube clamp 1802 may lack a gap 1806 in a variation where the tubing 1804 is threaded directly through the open region 1808. In further variations, the indicator device 100 of FIG. 1 or other variation of the indicator device has a tube clamp 1802 as a fastener.

Figure 19:
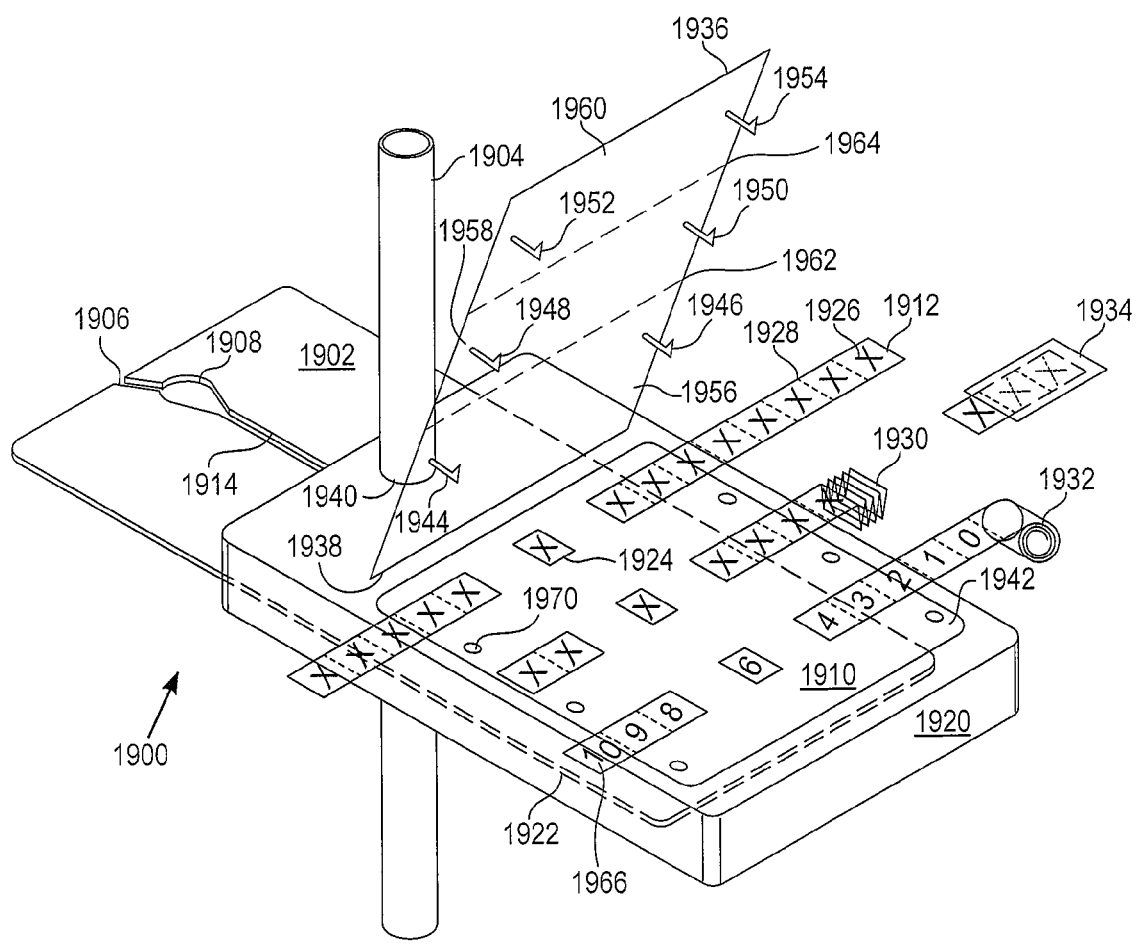
FIG. 19 is a perspective view of a still further variation of the manually settable indicator device of FIG. 9, having a tube clamp and a transparent cover.

With reference to FIG. 19, an indicator device 1900 with a tube clamp 1902 includes further features as compared to the indicator device 1800. A tube clamp 1902, having a tube attachment device and a tube pinch member, is included in the indicator device 1900. The tube clamp 1902 is similar in features and operation to the tube clamp 1802, and further slides along, into or out of or otherwise relative to an indicator mounting 1920, for example along a groove 1922. A gap 1906, an open region 1908 and a pinch region 1914 are positioned and act equivalently to the corresponding features of the tube clamp 1802. The mounting 1922 includes a pointer member 1910 and an indicia member 1912. The pointer member 1910 includes at least one window 1924 or other pointing area, and the indicia member 1912 includes at least one sliding strip 1926 with indicia alignable to the pointing area, functioning similarly to the indicator device 900 of FIG. 9. Sliding strips, such as the sliding strip 1926, slide relative to a respective window 1924 or other pointer of the pointer member 1910. The sliding strip 1926 may have perforations 1928, which are used for tearing off excess strip length after an indication is set. An at least partially transparent cover 1936 is hinged 1938 or has one or more pivot points closest to the tube attachment device, which may be a "C" clamp or an aperture 1940 through the mounting 1920 and through which the tubing 1904 is fed. A set indication may be viewed through a transparent portion of the cover 1936. A tube clamp 1902 or other tube pinch member, such as is known or readily devised by a person skilled in the art, slides and pinches the tube. The sliding strip 1926 and pointer member 1910 are mounted to a top surface 1942 of the device generally perpendicular to the tube 1904 to which the device may be attached. The transparent cover 1936 is hinged 1938 or otherwise pivots closest to the tube attachment device, and closes by fastening with at least one of pins 1944, 1946, 1948, 1950, 1952 and 1954 to cover the sliding strip 1926 or strips after the indication is set. Any or all of the pins 1944, 1946, 1948, 1950, 1952 and 1954 may have a barb or other one-way head so that the pin locks in the respective receiving aperture e.g. locking pin 1944 of the transparent cover 1936 is securable to the receiving aperture 1970 of the pointer member 1910.

In a variation, the transparent cover 1936 has multiple segments 1956, 1958 and 1960, each of which is hinged to any adjacent segment, for example by a living hinge 1962 and 1964. Each segment 1956, 1958 and 1960 of the multiple segmented transparent cover 1936 has one or two pins, e.g. pin 1944 or pins 1944 and 1946 for segment 1956. Thus, each segment, starting with the segment 1956 closest to the tube attachment device, may be fastened over a respective set indication of a respective sliding strip e.g. sliding strip 1926, allowing each sliding strip and respective indication to be locked in place with the pins of the respective segment of the transparent cover in sequence. Such a mechanism can be used to sequentially lock any set indications, leaving remaining strips slidable for further setting of indications. In a variation, each segment of the multiple segmented transparent cover 1936 is securable to the pointer member or the indicia member. In a further variation the outermost sliding strip is a counting strip 1966, and has numbers counting up or down.

Each time the counting strip is slid over by one or more counting numbers, the excess lengths of the counting strip 1966, including any counting numbers previously used, may be torn off, thus providing a record of how many times the device has been used or other event has occurred. Prior to setting the indication, in one variation the unused portions of the sliding strips are folded in an accordion fold and secured adjacent to the window or other pointer. A pocket, an envelope, a folded packaging member with a peel away backing, or other container 1934 with an interior region may be used for stowing the unused portions of the sliding strips in an accordion folded, coiled, rolled or other compact storage arrangement when the device is in an initial condition. An end of a sliding strip may be accordion-folded 1930, coiled or rolled 1932 and/or dispensed from the container 1934, which may be separate from or integrated with the mounting 1920. In a still further variation, a one-way mechanism such as the ratchet mechanism 1000 of FIG. 10 may be used for a counting device as a portion of the indicator device.

Figure 20:
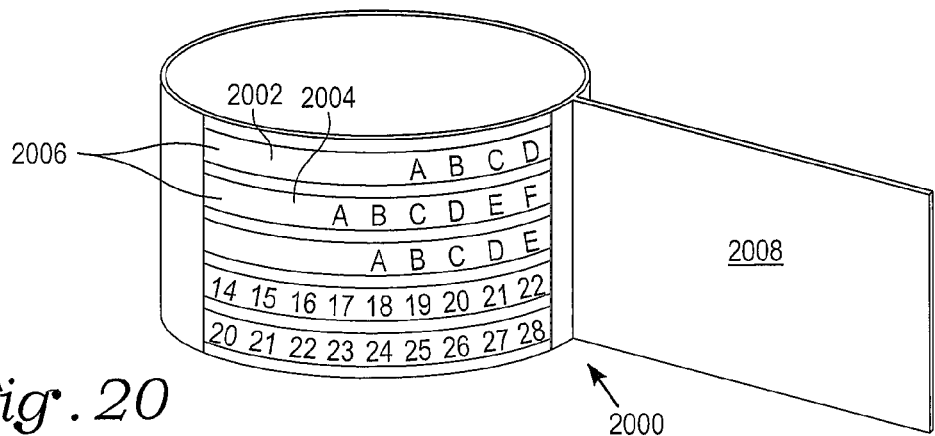
FIG. 20 is a perspective view of a variation of the manually settable indicator device of FIGS. 7A, 7B and 14, having sliding rings.
Figure 21:
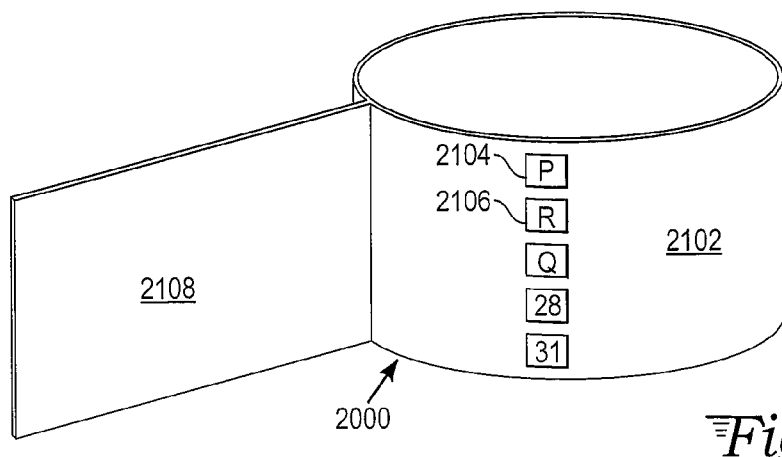
FIG. 21 is an alternate perspective view of the manually settable indicator device of FIG. 18.

With respect to FIGS. 20 and 21, an indicator device 2000 having a generally cylindrical shape may be considered a variation of the indicator device 700 of FIGS. 7A and 7B in that both devices have rotating rings. Further, the indicator device 2000 may be considered a variation of the indicator device 1400 of FIGS. 14 and 15, in that both devices have sliding strips. In the indicator device 2000, the rings are strips and the strips are rings. An indicia member 2006 has one or more rotating rings 2002 and 2004 with indicia. A pointer member 2102 has one or more windows 2104 and 2106 or other pointer areas. The indicia member 2006 moves relative to the pointer member 2102 such that indicia of the indicia member 2006 may be positioned relative to the windows 2104 and 2106. An adhesive section 2008 functions as a tamper resistant locking mechanism. The adhesive section 2008, which may have a removable backing protecting the adhesive section from inadvertently sticking to the device or another object prior to the setting of an indication, is folded over and adhered to a portion of the indicia member, such as the exposed portions of the rotating rings 2002 and 2004. The adhesive section 2008 may also adhere to a portion of the pointer member 2002 or a portion of a structure supporting the rotating rings or the pointing member, such as to material between the rotating rings or covering the enclosed portions of the rotating rings, fixing the setting of the indicia member 2006 relative to the pointer member 2102. In a variation, an adhesive section 2108 folds over the windows 2104 and 2106 and adheres to a portion of the indicia member 2006 at the window 2104 or the window 2106, fixing the setting of the indicia member 2006 relative to the pointer member 2102. The indicator device 2000 can be installed around tubing, flattened and slid along the tube. Rotating rings and sliding strips may be combined in a variation of the indicator device.

Figure 22:
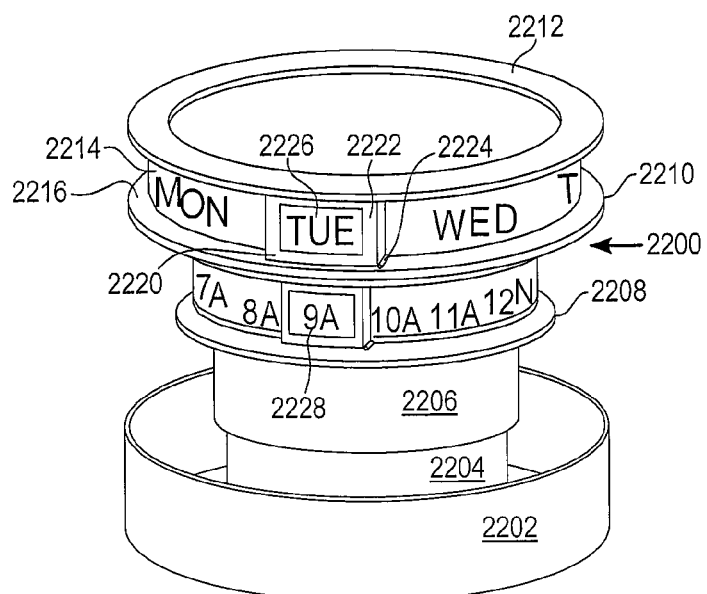
FIG. 22 is a perspective view of a further variation of the manually settable indicator device of FIGS. 7A, 7B and 14, having sliding rings and collapsing or extending for storage or display.

With respect to FIG. 22, a collapsing and extending indicator device 2200 has sliding, rotating rings and may be referred to as the camping cup or accordion embodiment. As in a known collapsible and extensible camping cup, successively sized rings 2204, 2206, 2208 and 2210 of the indicator device 2200 can extend upwards from a base 2202 or collapse downwards to the base 2202, each intermediate ring 2206 telescoping outside of a lower ring 2204 or inside of an upper ring 2208, the lowermost ring 2204 attaching to the base 2202 and the uppermost ring 2210 establishing the upper rim 2212 of the device. To make this collapsible device an indicator device 2200, one or more of the collapsing rings 2204, 2206, 2208 and 2210 has a further sliding ring 2214, for example a sliding ring 2214 rotating within a groove 2216 in the collapsing ring 2210. An indication is set by rotating the sliding ring 2214 relative to the collapsible ring 2210. An indicator member 2220, for each collapsing ring 2210 and companion sliding ring 2214, includes a windowed section 2222 mounted on one or more pins 2224 to the collapsing ring 2210 and allowing clearance for the sliding ring 2214. The windowed section 2222 may have one, two or four or another number of pins 2224, for example on corners or opposing sides of the windowed section. After the indication is set, the windowed section 2222 is pressed on to the collapsing ring 2210, securing the sliding ring 2214 by friction or by e.g. companion detents in the sliding ring 2214 and windowed section 2222. The device may be collapsed or extended before or after setting the indication, for storage or compact deployment, with the extended state being used for setting the indication or displaying the set indication. In a variation, the windowed section 2222 slides relative to the collapsing ring 2210, such as within a groove 2216 in the collapsing ring 2210, or is removable and replaceable to the collapsing ring 2210. Thus, a portion of the pointer member, namely the windowed section 2222, is movable relative to the collapsing ring 2210. Indicia, such as days of the week 2226, hours of the day 2228 or other markings may be made on a sliding ring 2214 when the indicator member 2220 does not slide around a collapsible ring 2210, 2208, 2206 or 2204, or on a collapsing ring 2210, 2208, 2206 or 2204 when the indicator member 2220 is slidable or otherwise positionable around a collapsing ring. Variations of the indicator device may collapse or extend with the use of hinges or other fold up or fold out mechanisms.

FIGS. 23-26 show fittings suitable for use with the indicator device of FIG. 1 or variations thereof.

Figure 23:
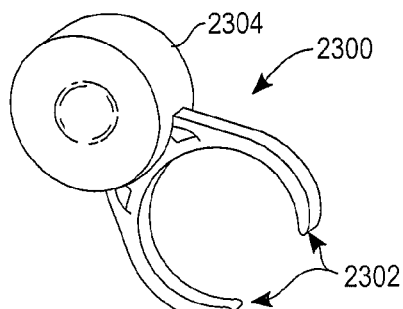
FIG. 23 is a perspective view of a "C" clamp suitable for use as a fastening device for the indicator device of FIG. 1 and variations.

With reference to FIG. 23, a "C" clamp 2300 may be used as a fastening device for an indicator device, and may be made of rigid or flexible material. The "C" clamp slips onto flexible tubing, or a flexible version of a "C" clamp slips onto rigid tubing or other tube structure. A base 2304 of the "C" clamp may be placed symmetrically or asymmetrically with respect to the jaws 2302, and various shapes for a base may be used as is known in the art. Generally, the jaws 2302 partially encircle the tubing, describing approximately two thirds or three quarters of a circle or at least one half of a circle so that the tubing is constrained within the jaws as a clip or a clamp.

Figure 24:
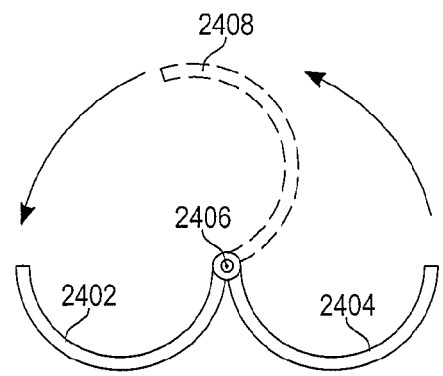
FIG. 24 is a perspective view of a hinged or double "C" clamp suitable for use as a fastening device for the indicator device of FIG. 1 and variations.

With reference to FIG. 24 a two-part, hinged "C" clamp 2400 may be used as a fastening device for an indicator device, and may be made of rigid or flexible material. A hinge, pin or other type of pivot 2406 joins the jaws 2402 and 2404, allowing either jaw to be moved relative to the other jaw. The pivot 2406 may provide friction so that an open or a closed position of the jaws 2402 and 2404 is maintained and/or one or both jaws 2402 and 2404 may describe more than one half of a circle as in the "C" clamp 2300, so that when closed, the hinged "C" claim 2400 remains attached to a tubing or an article. The hinged "C" clamp is applied around tubing, a tube or other article attachment area, and the jaws 2402 and 2404 are moved from the open position (as shown in FIG. 24) to a closed position similar to that of the "C" clamp 2300. Jaw 2404 is shown with dashed lines in an intermediate position 2408. A base or other connection from the hinged "C" clamp 2400 to an indicator device may be formed as a portion of or attached to either of the jaws 2402 and 2404, or may be attached to the pivot 2406.

Figure 25:
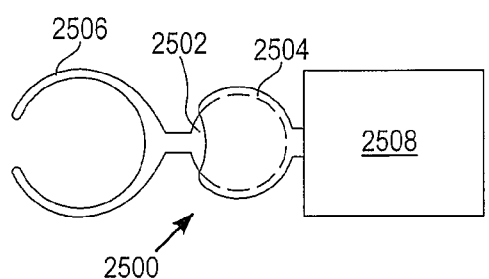
FIG. 25 is a perspective view of a "C" clamp and a ball and socket joint suitable for use as a fastening device for the indicator device of FIG. 1 and variations.

With reference to FIG. 25, a ball and socket joint 2500 may be used as a mount or a portion of a fastener for an indicator device 2508. A ball joint may be attached to a "C" clamp or other clamping device, and an embodiment of the indicator device mounted to the ball joint. With such a ball joint mounting, the indicator device can pivot, swivel, twist, flip and otherwise move relative to an article to which the indicator device is mounted. A "C" clamp or other clamp suitable for mounting to tubing further allows the indicator device to swivel around the tubing. A ball 2502 fits within a socket 2504 with sufficient tightness and friction so as to allow relative movement such as pivoting and rotation yet frictionally maintain a relative position of the indicator device 2508 and a clamp 2506 or other fastener. Other shapes may be devised, such as the socket being a sunken hollow beneath a surface aperture, the socket having a slot for a specific positioning of a shaft of the ball, the ball or a support for the ball having one or more protrusions to limit movement and so on. The ball 2502 may be attached to the clamp 2506 or other fastener, with the socket 2504 attached to the indicator device 2508, or the socket 2504 may be attached to the clamp 2506 or other fastener, with the ball 2502 attached to the indicator device 2508. In a variation, the ball 2502 is removable from the socket 2504, and the ball may be snapped into the socket. In a further variation, the ball or the socket is attached to an article, a first indicator device having an opposing socket or ball is unsnapped from the article, and a replacement indicator device having a further opposing socket or ball is snapped onto the article, using the ball and socket mechanism. Such an arrangement is especially useful when the indicator device is integrated with a disposable article such as a medical device with a limited lifespan, the indicator device being set to display an expiration date of the medical device. A replacement medical device with included indicator device may then be swapped in as the first medical device expires and is removed for disposal.

Figure 26:
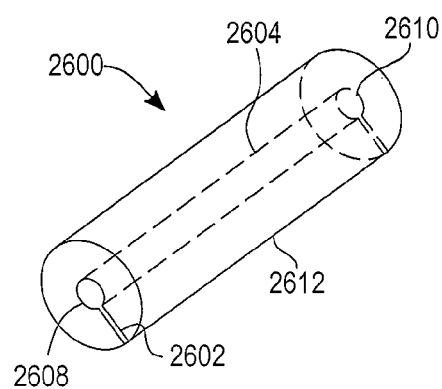
FIG. 26 is a perspective view of a sleeve having multiple uses with the indicator device of FIG. 1 and variations.

With reference to FIG. 26, a sleeve 2600 may be dimensioned according to a usage with an indicator device. In one variation, the sleeve 2600 is a split tube having a slit 2602 running the length of the tube and connecting from a hollow volume 2604 within the tube to one edge 2612 of the tube. The tube has openings 2608 and 2610 at opposing ends of the tube section. The split tube may be used as a fastening device, such as a tube clamp for an indicator device, with medical tubing inserted through the slit 2602 and retained within the hollow volume 2604. In a further variation, the sleeve 2600 is made of a soft, cushioning material such as foam, and is fastened around a portion or all of an indicator device to protect, for example, a medical patient from chafing as a result of contact with the indicator device. In a still further variation, the sleeve 2600 is made of a resilient, transparent material so that an indication displayed on the indicator device is visible through the sleeve 2600. In still further variations, one or both ends of the sleeve 2600 may be open or closed off, and other shapes may be devised. For example, a casing having an opening and a pocket may be made by folding material and sealing along one or more edges such as with glue, adhesive or hook and loop fasteners, and the casing may be applied as a sleeve for the indicator device. Such a casing or a sleeve may have a transparent region for viewing a setting of the indicator device, and may have padding for preventing chafing of a patient or for protecting the device itself.

Figure 27:
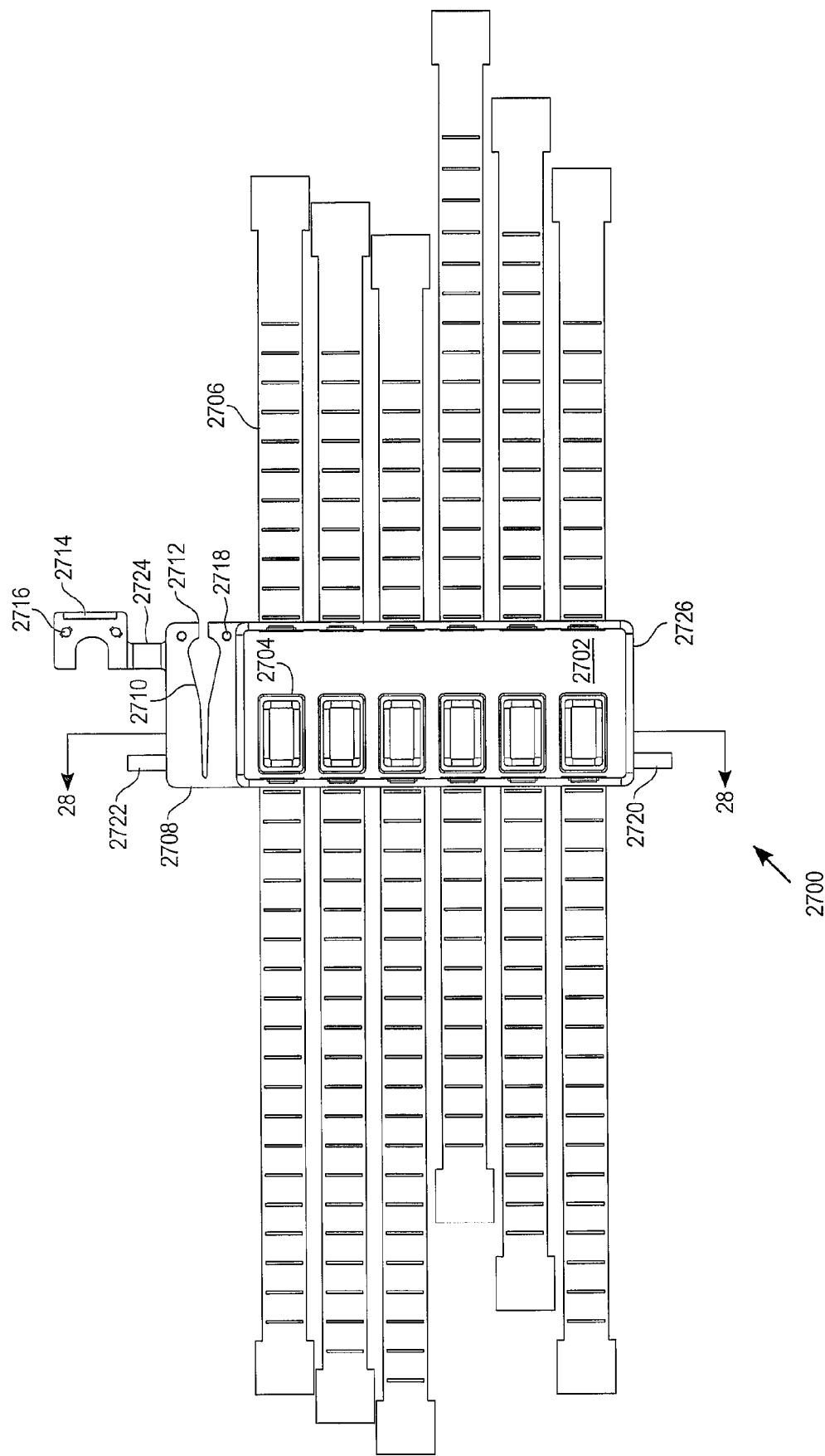
FIG. 27 is a bottom elevated view of a variation of the indicator device of FIGS. 14-19.

With reference to FIG. 27, a further variation of the indicator device of FIGS. 14-19 is shown. The indicator device 2700, as seen in the bottom view of FIG. 27, has a back side 2702 with a crush region 2704 for locking a sliding strip 2706, as will be further described with reference to FIG. 28.

A tube clamp 2708, related to the tube clamp 1802 shown in the indicator device 1800 of FIG. 18, is used for fastening the indicator device 2700 to medical or other tubing. The tube clamp 2708 has an aperture 2710 with a gap 2712 and may have an open region and a pinch region similar to that of the tube clamp 1802. After tubing is inserted through the gap 2712 into the tube clamp 2708, a locking clamp 2714 with at least one locking pin 2716 is secured to the tube clamp 2708, as by inserting the locking pin 2716 into an aperture 2718 of the tube clamp 2708. In one example, the tube clamp 2708, the locking clamp 2714, at least one locking pin 2716 and a living hinge 2724 attaching the locking clamp 2714 to the tube clamp 2708 are molded as a unitary body which may further be a unitary body with the pointer member 2726 of the indicator device 2700. Thus, the tube clamp 2708 provides a locking or lockable, tamper resistant or tamper evident mechanism for attaching the indicator device 2700 to tubing. Variations of the tube clamp 2708, including a slide clamp, a roller clamp or a pinch clamp, may be devised for attaching to other articles. The indicator device 2700 may be equipped with tubing splice fittings 2720 and 2722, as a variation for attaching to tubing.

Figure 28:
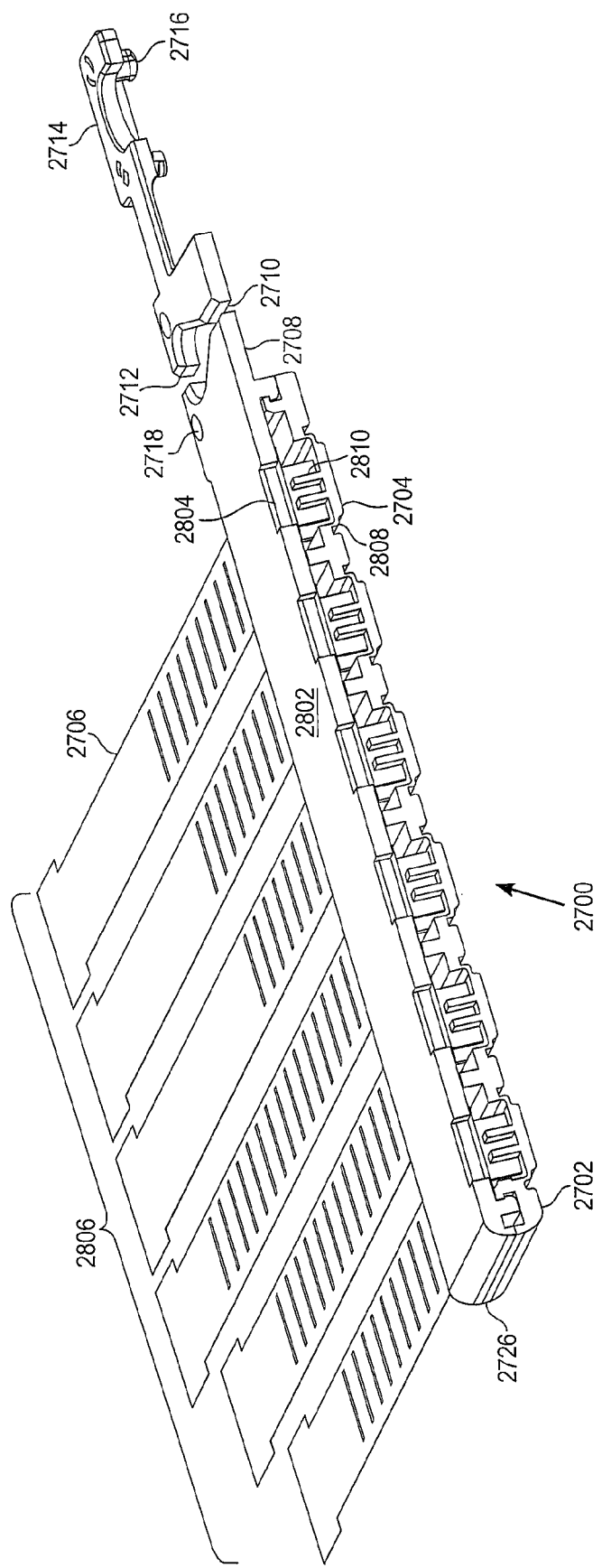
FIG. 28 is a perspective cutaway view of the indicator device of FIG. 27.

With reference to FIG. 28, a cross-section of the indicator device 2700 is shown. The front side 2802 of the pointer member 2726 has at least one pointing area 2804, which may be a window through which a portion of the sliding strip 2706 is visible. In operation, the sliding strip 2706, as a portion of the indicia member 2806, is moved relative to the pointer member 2726 in a manner related to the operation of previously described sliding strips versions of the indicator device. To freeze or lock the indication, as by locking at least a portion of the indicia member relative to the indicator member, the crush region 2704, accessed from the back side 2702, is pressed towards the front side 2802, deforming at least one deformation member 2808. Further, at least one pin 2810 or other projection from a portion of the crush region 2704 pierces a portion of the sliding strip 2706 and may lodge in a portion of the pointer member 2726. In a variation, the at least one pin 2810 inserts through a precut aperture or slot in the sliding strip 2706. The pin 2810 locks the sliding strip 2706, preventing alteration of the positioning of the sliding strip. Damage to the sliding strip 2706, the crush region 2704 and/or the deformation member 2808 provides evidence of tampering attempts. Thus, the indicator device 2700 provides a tamper resistant or tamper evident mechanism for locking the setting or the indication i.e. locking the indicia member relative to the pointer member 2726. A variation of the indicator device uses a ratchet mechanism such as shown in FIG. 10.

Being manually settable and tamper resistant, the indicator device offers a tool to reduce errors and contamination in a medical environment, providing a visual reminder of change out requirements or other pertinent information about equipment or a product to which it is attached. Such information may relate to a supply, a device, equipment, an operator and/or a patient. Accuracy of communication is improved and transfer of contaminants, especially infectious agents, is reduced as compared to the use of manually written adhesive labels. In medical professions and settings, the indicator device may have use under Unique Device Identification (UDI) and/or Automatic Identification and Data Capture (AIDC) rules and regulations. The indicator device has uses in other professions as well, improving safety, communication, efficiency and ease of use of products to which the device is attached. Indicator devices may be made in various shapes having functional, commercial or aesthetic appearances appropriate to the area of use.

What is claimed is:

1. A method for visibly indicating information on a medical device attached to a medical patient, the method comprising:
   affixing an indicator device to a medical device;
   attaching the medical device to a medical patient;
   setting the indicator device to display information relating to the medical device and including a time, a day, a date, a usage count, a baseline information, or a personnel identifier, concomitantly with attaching the medical device to the medical patient;

employing a means for mechanically arresting an indicia member of the indicator device relative to a pointer member of the indicator device in a tamper resistant manner; and identifying the indicator device using a scannable identification device;

wherein setting the indicator device includes manually moving at least a portion of the indicia member relative to at least a portion of the pointer member.

2. The method of claim 1 further comprising sterilizing the indicator device.

3. The method of claim 1 wherein affixing the indicator device to the medical device includes adhering the indicator device to the medical device using an adhesive surface of the indicator device.

4. The method of claim 1 wherein affixing the indicator device to the medical device includes inserting a fastener through an aperture of the pointer member.

5. The method of claim 1 wherein affixing the indicator device to the medical device includes manufacturing the indicator device integrally with the medical device.

6. The method of claim 1 wherein the medical device is disposable and the date is a start date or an expiration date, relating to a usage of the medical device.

7. The method of claim 1 wherein the medical device includes one of: an intravenous tubing, an intravenous tubing valve, an intravenous tubing port, a medication container, a catheter, a dressing, an infusion equipment, a drain, a respiratory therapy device or a feeding tube.

8. The method of claim 1 wherein locking the displayed information includes adhering an adhesive surface of a locking member of the indicator device to at least one of the indicia member or the pointer member.

9. The method of claim 1 wherein manually moving at least a portion of the indicia member includes moving at least one of a plurality of sliding strips of the indicia member.

10. The method of claim 1 wherein setting the indicator device includes aligning selected indicia on sliding strips of the indicia member to a pointing area of the pointer member to display the information.

11. The method of claim 1 further including extending or collapsing at least a portion of the indicator device.

12. The method of claim 1 further including stacking a plurality of members or ones of the indicator device.

13. The method of claim 1 further including moving at least one member of the indicator device about a pivot point of the indicator device to form a fan arrangement.

14. The method of claim 1 wherein attaching the indicator device to a medical device includes attaching tubing of the medical device to a splice fitting of the indicator device.

15. The method of claim 1 wherein attaching the indicator device to a medical device includes fastening a locking clamp of the indicator device to the medical device.

16. The method of claim 1 wherein attaching the indicator device to a medical device includes fastening a tamper resistant clamp of the indicator device to the medical device.

17. The method of claim 1 wherein the indicator device includes a sliding resistant tubing clamp.

18. The method of claim 1 wherein attaching the indicator device to a medical device includes inserting a tubing of the medical device into a tubing clamp of the indicator device and securing the tubing using a locking mechanism.

19. The method of claim 1 wherein the information further includes a starting time, day or date or an expiration time, day or date.

20. The method of claim 1 wherein the information further includes a unit of measure, a location, or an identifier of person or a product.

21. The method of claim 1 wherein first and second portions of the indicia member or the pointer member are independently lockable.

22. An indicator device comprising:
an indicia member with a plurality of sliding strips having indicia thereupon;
a pointer member with at least one pointing area;
a tamper resistant locking member operable to fix at least a portion of the indicia member to at least a portion of the pointer member; and
a fastening device;
wherein each sliding strip is mounted to the pointer member and independently manually movable to display a respective selected one of the indicia at the pointing area;
wherein an adhesive surface of the locking member adheres to a portion of at least one sliding strip and to a portion of the pointer member.

23. The indicator device of claim 22 wherein each sliding strip enters a respective slit of the pointer member, displays the respective selected one of the indicia at the pointing area and exits a further respective slit of the pointer member.

24. The indicator device of claim 22 wherein the pointing area includes at least one window.

25. The indicator device of claim 22 wherein the pointing area includes at least one of an arrow, a symbol, a line segment or text.

26. The indicator device of claim 22 further including a barcode, an RFID or a microchip.

27. The indicator device of claim 22 wherein the locking member includes a transparent portion through which the selected indicia are visible upon adhering an adhesive surface of the locking member to a front side of the pointer member.

28. The indicator device of claim 22 wherein the fastening device includes an adhesive surface on a back side of the pointer member.

29. The indicator device of claim 22 wherein the fastening device includes an aperture of the pointer member through which a fastener is insertable.

30. The indicator device of claim 22 further comprising the indicator device being in a sterile condition within a sterile packaging.

31. The indicator device of claim 22 further comprising at least a portion of the indicator device being extendable or collapsible.

32. The indicator device of claim 22 further comprising at least a portion of the indicator device being stackable and having at least a pin for stacking.

33. The indicator device of claim 22 further comprising pivoting members deployable to a fan arrangement.

34. The indicator device of claim 22 wherein the fastening device further includes a tubing splice fitting.

35. The indicator device of claim 22 wherein the fastening device further includes a locking clamp having at least a locking pin.

36. The indicator device of claim 22 wherein the fastening device further includes a tamper resistant clamp.

37. The indicator device of claim 22 wherein the fastening device further includes a tubing clamp having at least one finger.

38. The indicator device of claim 22 wherein the fastening device further includes a slidable tubing clamp having a pinch region, a tubing insertion gap and a lockable mechanism to secure a tubing in the slidable tubing clamp.

39. The indicator device of claim 22 wherein the locking member includes a crush region or a deformation member.

40. The indicator device of claim 22 wherein a one of the plurality of sliding strips is lockable independently of a further one of the plurality of sliding strips.

41. The indicator device of claim 22 further comprising a container in which an unused portion of a one of the plurality of sliding strips is stowed.

* * * * *